United States Patent
Bell et al.

(10) Patent No.: US 8,778,984 B2
(45) Date of Patent: Jul. 15, 2014

(54) ALDOSTERONE SYNTHASE INHIBITOR

(75) Inventors: Michael Gregory Bell, Fishers, IN (US); Paul J. Hoogestraat, Indianapolis, IN (US); Thomas Edward Mabry, Indianapolis, IN (US); Quanrong Shen, Fishers, IN (US); Ana Maria Escribano, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/490,530

(22) Filed: Jun. 7, 2012

(65) Prior Publication Data
US 2012/0322841 A1    Dec. 20, 2012

Related U.S. Application Data

(60) Provisional application No. 61/496,657, filed on Jun. 14, 2011, provisional application No. 61/506,349, filed on Jul. 11, 2011.

(51) Int. Cl.
 *C07D 231/56* (2006.01)

(52) U.S. Cl.
 USPC .................................. 514/406; 548/360.1

(58) Field of Classification Search
 None
 See application file for complete search history.

(56) References Cited

U.S. PATENT DOCUMENTS

| 5,057,521 A | 10/1991 | Haeusler et al. |
| 2007/0049616 A1 | 3/2007 | Ksander et al. |

FOREIGN PATENT DOCUMENTS

| EP | 0165904 | 12/1985 |
| JP | 57165369 | 10/2012 |
| WO | 2007024945 | 3/2007 |
| WO | 2011064376 | 6/2011 |
| WO | WO2011088188 | 7/2011 |

OTHER PUBLICATIONS

Patani et al ,Chemical Reviews, 1996, vol. 96, No. 8, p. 3152.*
Database Caplus (Online), Chemical Abstracts Service, "Pyrazole derivatives," XP002679479; Database accession No. 1983: 72088 (1983).

* cited by examiner

*Primary Examiner* — Kamal Saeed
(74) *Attorney, Agent, or Firm* — Elizabeth A. Dingess-Hammond

(57) ABSTRACT

The present invention provides aldosterone synthase inhibitors of the formula:

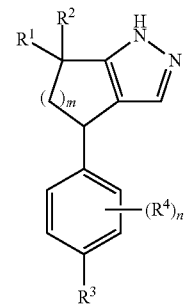

Figure 1:
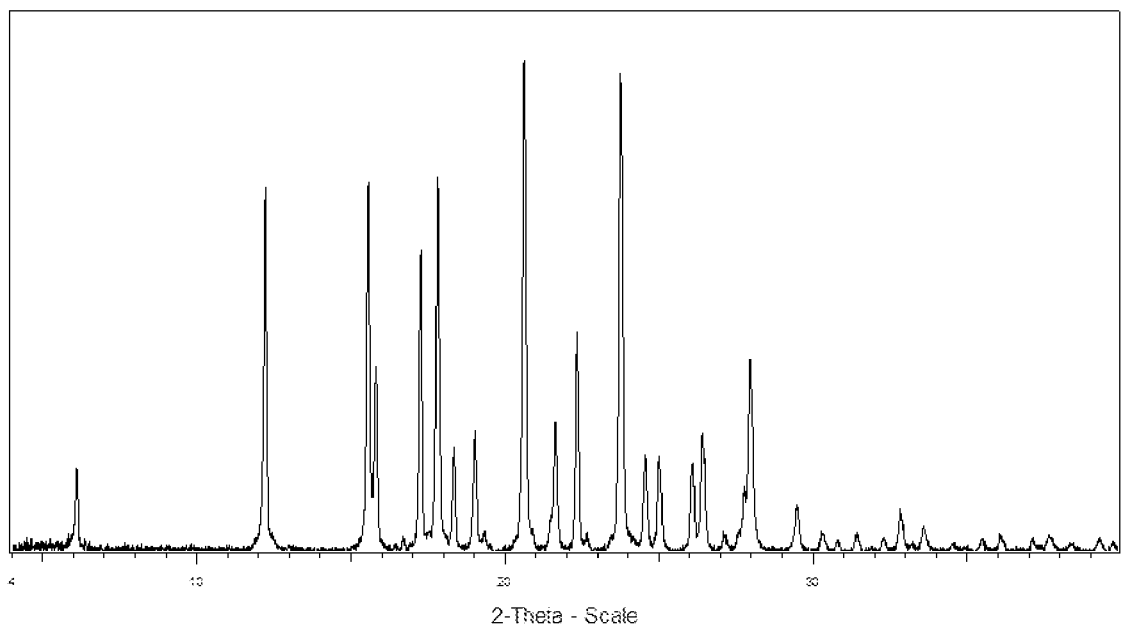

intermediates, methods for their preparation, pharmaceutical preparations, and methods for their use.

18 Claims, 2 Drawing Sheets

X-ray powder diffraction pattern of Example 1a, 4-[(4R)-6,6-dimethyl-4,5-dihydro-1H-cyclopenta[c]pyrazol-4-yl]benzonitrile hemihydrates X-ray powder diffraction pattern of Example 1b, 4-[(4R)-6,6-dimethyl-4,5-dihydro-1H-cyclopenta[c]pyrazol-4-yl]benzonitrile; phosphoric acid

ALDOSTERONE SYNTHASE INHIBITOR

This application claims priority to the following: U.S. Provisional Patent Application No. 61/496,657 filed on Jun. 14, 2011 and U.S. Provisional Patent Application No. 61/506,349 filed on Jul. 11, 2011, each hereby incorporated by reference in their entirety.

The present invention relates to compounds and salts useful for inhibiting aldosterone synthase and pharmaceutical compositions thereof.

Aldosterone synthase is the rate limiting enzyme for the production of aldosterone. Elevated plasma aldosterone levels have been associated with progressive renal disease leading to chronic kidney disease. Infusion of aldosterone in rats has been observed to produce kidney fibrosis and elevated proteinuria—a marker for kidney damage. Animal models of kidney disease have shown that aldosterone synthase inhibitors are useful for the treatment of kidney disease.

The main causes of kidney disease are diabetes leading to diabetic nephropathy and hypertension. Aldosterone synthase inhibitors have also been shown to be useful for the treatment of resistant hypertension particularly when combined with angiotensin converting enzyme (ACE) inhibitors or angiotensin receptor blockers (ARBs). Studies have also shown significantly elevated levels of aldosterone in patients with congestive heart failure (CHF). Aldosterone blockade has been shown to improve survival in patients with CHF.

Aldosterone synthase inhibitors have been disclosed in, for example, U.S. Pat. No. 5,057,521 and European Patent Publication number 0 165 904. Aldosterone synthase inhibitor compounds have the potential to also inhibit production of cortisol, testosterone and/or estradiol. Inhibition of cortisol, testosterone and/or estradiol is an undesired side effect of current aldosterone synthase inhibitors. Thus, there is a need to discover new aldosterone synthase inhibitors. Additionally, the need also exists to discover new aldosterone synthase inhibitors that selectively inhibit production of aldosterone compared to the inhibition of cortisol, testosterone and/or estradiol production.

The present invention provides alternate aldosterone synthase inhibitors. Also, the present invention provides compounds that may selectively inhibit aldosterone production compared to production of cortisol, testosterone and/or estradiol.

The present invention provides a compound of the formula:

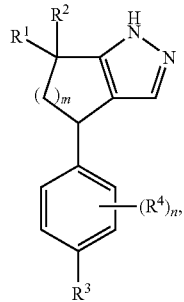

wherein
n is 0, 1, or 2;
m is 1 or 2;
$R^1$ and $R^2$ are independently selected from hydrogen, —$CH_3$, and —$CH_2CH_3$;
$R^3$ is hydrogen, —CN, —F, —Cl, —$CH_3$, —$OCH_3$, or —$CF_3$;
$R^4$ is at each instance independently selected from —F, —Cl, —Br, —$CH_3$, —$OCH_3$, —$CF_3$, and —CN;
or a pharmaceutically acceptable salt thereof.

The present invention provides a method of treating chronic kidney disease comprising administering an effective amount of a compound of the invention or a pharmaceutically acceptable salt thereof to a patient in need thereof.

The present invention also provides a method of treating diabetic nephropathy comprising administering an effective amount of a compound of the invention or a pharmaceutically acceptable salt thereof to a patient in need thereof.

The present invention further provides a method of treating congestive heart failure or hypertension comprising administering an effective amount of a compound of the invention or a pharmaceutically acceptable salt thereof to a patient in need thereof.

The present invention additionally provides a pharmaceutical composition comprising a compound of the invention or a pharmaceutically acceptable salt thereof, and one or more pharmaceutically acceptable carriers, diluents, or excipients. In a particular embodiment, the composition further comprises one or more other therapeutic agents.

Further, the present invention also provides compounds of the invention or pharmaceutically acceptable salts thereof for use in therapy, in particular for the treatment of chronic kidney disease, diabetic nephropathy, congestive heart failure, or hypertension.

Furthermore, the present invention provides compounds of the invention or pharmaceutically acceptable salts thereof for use in the treatment of chronic kidney disease. The present invention also provides compounds of the invention or pharmaceutically acceptable salts thereof for use in the treatment of diabetic nephropathy. The present invention further provides compounds of the invention or pharmaceutically acceptable salts thereof for use in the treatment of congestive heart failure and hypertension.

Even further, the present invention provides the use of a compound of the invention or a pharmaceutically acceptable salt thereof for the manufacture of a medicament for the treatment of chronic kidney disease, diabetic nephropathy, congestive heart failure, or hypertension.

The present invention also provides a method of treating chronic kidney disease comprising co-administering effective amounts of a compound of the invention and one or more of an angiotensin-converting enzyme inhibitor (ACE inhibitor), an angiotensin receptor blocker (ARB), or a mineralocorticoid receptor (MR) antagonist. ACE inhibitors include benazepril (marketed in the U.S. as Lotensin®), captopril (marketed in the U.S. as Capoten®), enalapril/enalaprilat (marketed in the U.S. as Vasotec® oral and injectable), fosinopril (marketed in the U.S. as Monopril®), lisinopril (marketed in the U.S. as Zestril® and Prinivil®), moexipril (marketed in the U.S. as Univasc®), perindopril (marketed in the U.S. as Aceon®), quinapril (marketed in the U.S. as Accupril®), ramipril (marketed in the U.S. as Altace®), and trandolapril (marketed in the U.S. as Mavik®). ARBs include candesartan (marketed in the U.S. as Atacand®), irbesartan (marketed in the U.S. as Avapro®), olmesartan (marketed in the U.S. as Benicar®), losartan (marketed in the U.S. as Cozaar®), valsartan (marketed in the U.S. as Diovan®), telmisartan (marketed in the U.S. as Micardis®), and eprosartan (marketed in the U.S. as Teveten®). The present invention further provides a method of treating diabetes or hypertension or congestive heart failure comprising co-administering effective amounts of a compound of the invention and a diuretic. Diuretics include torsemide (marketed in the U.S. as Demadex®), furosemide (marketed in the U.S. as Lasix®), bumetanide (marketed in the U.S. as Bumex®), ethacrynic acid (marketed in the U.S. as Edecrin®), torsemide (marketed in the U.S. as Demadex®), amiloride, (marketed in the U.S. as Midamor®), acetazolamide (marketed in the U.S. as Diamox®), pamabrom (marketed in the U.S. as Aqua-Ban®), mannitol (marketed in the U.S. as Aridol® or Osmitrol®), traimterene (marketed in the U.S. as Dyrenium®), spironolactone (marketed in the U.S. as Aldactone®), amiloride (marketed in the U.S. as Midamor®), indapamide (marketed in the U.S. as Lozol®), hydrochlorothiazide (marketed in the U.S. as HydroDIURIL®), metolazone (marketed in the U.S. as Zaroxolyn® or Mykrox®), methylclothiazide (marketed in the U.S. as Aquatensen® or Enduron®), hydrocholorthiazide (marketed in the U.S. as Aquazide H® or Esidrix® or Microzide®), chlorothiazide (marketed in the U.S. as Diuril®), bendroflumethiazide (marketed in the U.S. as Naturetin®), polythiazide (marketed in the U.S. as Renese®), hydroflumethiazide (marketed in the U.S. as Saluron®), and chlorthalidone (marketed in the U.S. as Thalitone®). For a complete listing also see, e.g., *Physician's Desk Reference*, 2012 Edition, PDR Network (2011).

Figure 2:
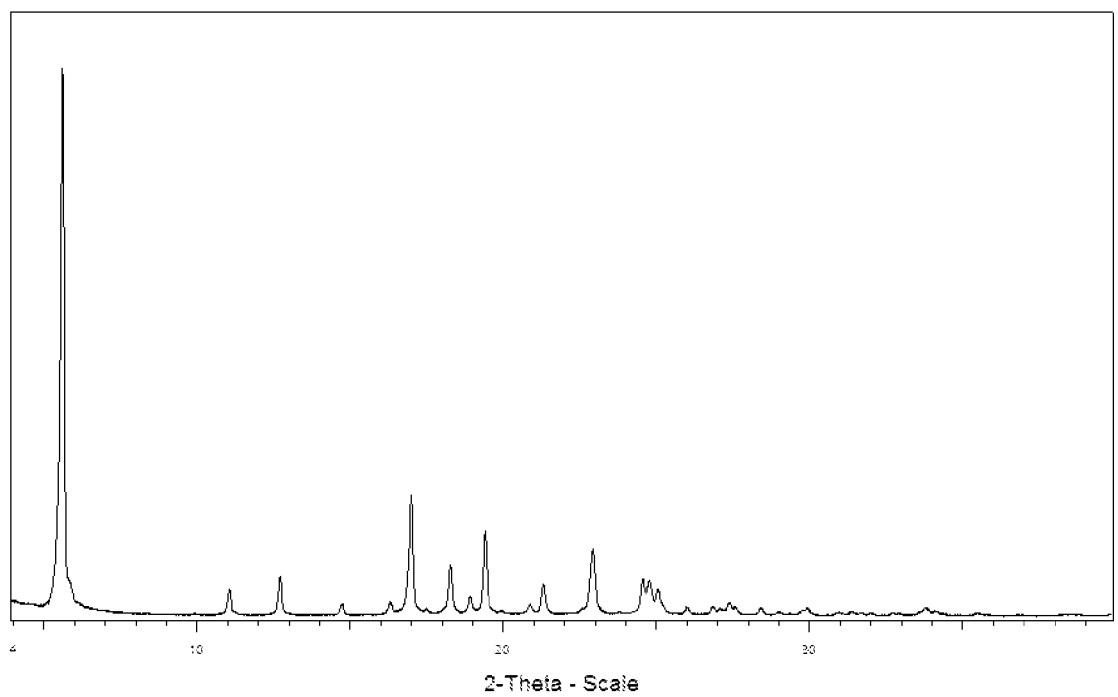

FIG. 1 is a spectrogram of a representative X-ray powder diffraction (XRD) pattern for 4-[(4R)-6,6-dimethyl-4,5-dihydro-1H-cyclopenta[c]pyrazol-4-yl]benzonitrile hemihydrates. The XRD spectrogram was obtained as described in the Example 1a below. FIG. 2 is a spectrogram of a representative XRD pattern for 4-[(4R)-6,6-dimethyl-4,5-dihydro-1H-cyclopenta[c]pyrazol-4-yl]benzonitrile; phosphoric acid. The XRD spectrogram was obtained as described in the Example 1b below.

The term "nitrogen protecting group" is taken to mean a moiety that is stable to projected reaction conditions and yet may be selectively removed by reagents and reaction conditions compatible with the regenerated amine Such groups are well known by the skilled artisan and are described in the literature. See, e.g., Greene and Wuts, *Protective Groups in Organic Synthesis*, Third Edition, Chapter 7, John Wiley and Sons Inc., (1999).

The skilled artisan will appreciate that compounds of the invention can exist in tautomeric forms, as depicted below in I and I(a). When any reference in this application to one of the specific tautomers of the compounds of the invention is given, it is understood to encompass both tautomeric forms and all mixtures thereof.

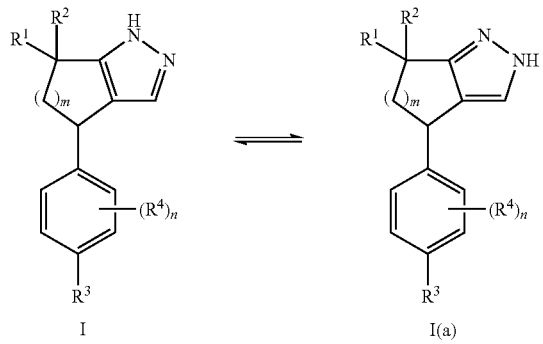

The skilled artisan will appreciate that compounds of the invention are comprised of a core that contains at least one chiral center, represented by "*" in I(b) below:

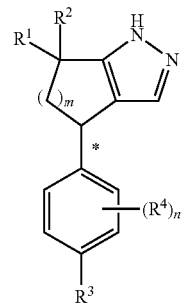

Although the present invention contemplates all individual enantiomers, as well as mixtures of the enantiomers of said compounds including racemates, the compounds with the absolute configuration as illustrated in I(c) below are preferred compounds of the invention.

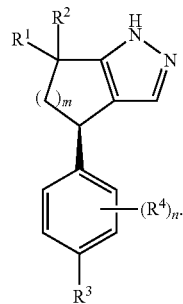

Isomers of compounds of the invention are labeled as isomer 1, isomer 2, etc., beginning with the first to elute (lower retention time) from the chromatographic separation method employed and disclosed herein.

Additionally, the skilled artisan will appreciate that additional chiral centers may be created in the compounds of the invention by the selection of certain variables. The present invention contemplates all individual enantiomers or diastereomers, as well as mixtures of the enantiomers and diastereomers of said compounds including racemates.

The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention.

The compounds of the present invention are cyclopentylpyrazoles or tetrahydroindazoles, and accordingly, react with any of a number of inorganic and organic acids to form pharmaceutically acceptable acid addition salts. Pharmaceutically acceptable salts and common methodology for preparing them are well known in the art. See, e.g., P. Stahl, et al. *Handbook of Pharmaceutical Salts: Properties, Selection and Use*, (VCHA/Wiley-VCH, 2002); S. M. Berge, et al., "Pharmaceutical Salts," *Journal of Pharmaceutical Sciences*, Vol. 66, No. 1, January 1977. Preferred pharmaceutically acceptable salts of the invention are those formed with hydrochloric acid or phosphoric acid.

The compounds of the present invention are preferably formulated as pharmaceutical compositions administered by a variety of routes. Most preferably, such compounds are for oral administration. Such pharmaceutical compositions and processes for preparing same are well known in the art. See, e.g., Remington: *The Science and Practice of Pharmacy* (A. Gennaro, et. al., eds., 19th ed., Mack Publishing Co., 1995).

The compounds of the present invention are generally effective over a wide dosage range. For example, dosages per day normally fall within the range of about 0.01 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

As used herein the terms "treating" and "treat" mean slowing or delaying the progression of a disease, such as kidney disease, in a patient in need thereof. Diabetes and hypertension are the two main causes of chronic kidney diseases. In many patients with chronic kidney disease, diabetes and hypertension co-exist. Diabetic patients with chronic kidney disease (diabetic nephropathy) are likely to have accelerated progress to ESRD. They are also at high risk of mortality, mostly due to cardiovascular complications such as heart disease. Chronic kidney disease is classified based on glomerular filtration rates wherein filtration rates decrease from Stage 1 though stage 5 or ESRD. For review of aldosterone synthase literature see, for example, See J. Am. Soc. Nephrol 14, 2395-2401 (2003); *Kidney International*, 21, 98-101 (1982); and *Circulation* 111, 3087-3094 (2005). As used herein the term "chronic kidney disease" refers to kidney disease that persists for more than three months.

As used herein, the phrase "effective amount" means an amount of a compound of the invention that is sufficient to treat in one or more doses a condition or detrimental effect thereof herein described or an amount of a compound of the invention that is sufficient to inhibit aldosterone synthase to achieve the objectives of the invention.

As used herein, the phrase "co-administering" means the administration of a compound of the invention and another compound described herein, separately, simultaneously or sequentially over a period of time as determined by a qualified care giver.

As used herein, "patient" refers to a mammal, preferably human.

Although all of the exemplified compounds of the invention are useful aldosterone synthase inhibitors, certain classes of compounds are preferred. The following paragraphs describe such preferred classes:

a) $R^1$ and $R^2$ are both $CH_3$;
b) $R^1$ and $R^2$ are both hydrogen;
c) $R^1$ is —$CH_3$ and $R^2$ is hydrogen;
d) m is 1;
e) m is 2;
f) $R^3$ is —CN;
g) $R^3$ is —F;
h) $R^3$ is —Cl;
i) $R^3$ is —$CH_3$;
j) $R^3$ is hydrogen;
k) n is 0;
l) n is 1;
m) n is 2;
n) $R^4$ is —F;
o) $R^4$ is —Cl;
p) $R^4$ is —Br;
q) $R^4$ is —$CH_3$;
r) $R^4$ is —CN;
s) the $R^4$ substituent is in the meta position relative to $R^3$;
t) $R^3$ is —CN and $R^4$ is —F;
u) $R^3$ is —CN and $R^4$ is —Cl;
v) $R^3$ is —F or —Cl and $R^4$ is —F, —Cl, or —Br;
w) $R^3$ is —$C^1$ and $R^4$ is —F;
x) $R^3$ is —Cl and $R^4$ is —Cl;
y) $R^3$ is —F and $R^4$ is —F;
z) $R^3$ is —F and $R^4$ is —Cl;
aa) The compound of the present invention is a free base;
bb) The compound of the present invention is the hydrochloride salt;
cc) The compound of the present invention is the phosphate salt.

A preferred embodiment of the compounds of the present invention relates to compounds of the invention of the following formula,

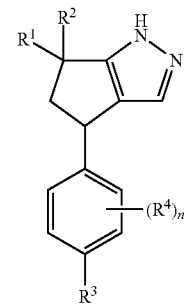

wherein n is 0, 1, or 2; $R^1$ and $R^2$ are independently selected from hydrogen, —$CH_3$, and —$CH_2CH_3$; $R^3$ is hydrogen, —CN, —F, —Cl, or —$CF_3$; $R^4$ is at each instance independently selected from —F, —Cl, —Br, —$CH_3$, —$CF_3$, and —CN; or a pharmaceutically acceptable salt thereof.

Another preferred embodiment of the compounds of the present invention relates to compounds of the invention of the following formula,

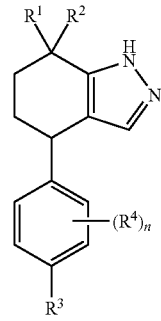

wherein n is 0 or 1; $R^1$ and $R^2$ are independently selected from hydrogen and —$CH_3$; $R^3$ is hydrogen, —CN, halo (Cl), —$OCH_3$, —$CH_3$; $R^4$ is at each instance independently selected from halo (F), —CH₃, and —OCH₃; or a pharmaceutically acceptable salt thereof.

A further preferred embodiment of the compounds of the present invention relates to compounds of the invention wherein n is 0 or 1; m is 1 or 2; $R^1$ and $R^2$ are independently selected from hydrogen, —CH₃, and —CH₂CH₃; $R^3$ is —CN; $R^4$ is at each instance independently selected from —F, —Cl, —Br, —CH₃, and —OCH₃; or a pharmaceutically acceptable salt thereof.

An additional preferred embodiment of the compounds of the present invention relates to compounds of the invention wherein n is 0 or 1; m is 1; $R^1$ and $R^2$ are independently selected from hydrogen, —CH₃, and —CH₂CH₃; $R^3$ is —CN; $R^4$ is —F, —Cl, or —Br; or a pharmaceutically acceptable salt thereof.

Another preferred embodiment of the compounds of the present invention relates to compounds of the invention wherein n is 0 or 1; m is 2; $R^1$ and $R^2$ are independently selected from hydrogen and —CH₃; $R^3$ is —CN; $R^4$ is —F, —Cl, —Br, —CH₃, or —OCH₃; or a pharmaceutically acceptable salt thereof.

A further preferred embodiment of the compounds of the present invention relates to compounds of the invention wherein n is 1; m is 1 or 2; $R^1$ and $R^2$ are independently selected from hydrogen and —CH₃; $R^3$ is —CN; $R^4$ is —F, —Cl, —Br, or —CH₃; or a pharmaceutically acceptable salt thereof.

An additional preferred embodiment of the compounds of the present invention relates to compounds of the invention wherein n is 1; m is 1; $R^1$ and $R^2$ are —CH₃; $R^3$ is —CN; $R^4$ is —F, —Cl, or —Br; or a pharmaceutically acceptable salt thereof.

Another preferred embodiment of the compounds of the present invention relates to compounds of the invention wherein n is 1; m is 2; $R^1$ and $R^2$ are independently selected from hydrogen and —CH₃; $R^3$ is —CN; $R^4$ is —F, —Cl, —Br, or —CH₃; or a pharmaceutically acceptable salt thereof.

A further preferred embodiment of the compounds of the present invention relates to compounds of the invention wherein n is 1; m is 1 or 2; $R^1$ and $R^2$ are —CH₃; $R^3$ is —CN; $R^4$ is —F; or a pharmaceutically acceptable salt thereof.

An additional preferred embodiment of the compounds of the present invention relates to compounds of the invention wherein n is 1; m is 2; $R^1$ and $R^2$ are —CH₃; $R^3$ is —CN; $R^4$ is —F; or a pharmaceutically acceptable salt thereof.

Another preferred embodiment of the compounds of the present invention relates to compounds of the invention wherein n is 0, 1, or 2; m is 1 or 2; $R^1$ and $R^2$ are independently selected from hydrogen and —CH₃; $R^3$ is —F or —Cl; $R^4$ is at each instance independently selected from —F, —Cl, —Br, —CH₃, and —CF₃; or a pharmaceutically acceptable salt thereof.

An additional preferred embodiment of the compounds of the present invention relates to compounds of the invention wherein n is 0, 1, or 2; m is 1; $R^1$ and $R^2$ are independently selected from hydrogen and —CH₃; $R^3$ is —F or —Cl; $R^4$ is at each instance independently selected from —F, —Cl, —Br, —CH₃, and —CF₃; or a pharmaceutically acceptable salt thereof.

A further preferred embodiment of the compounds of the present invention relates to compounds of the invention wherein n is 0, 1, or 2; m is 2; $R^1$ and $R^2$ are independently selected from hydrogen and —CH₃; $R^3$ is —F or —Cl; $R^4$ is at each instance independently selected from —F, —Cl, —Br, —CH₃, and —CF₃; or a pharmaceutically acceptable salt thereof.

Another preferred embodiment of the compounds of the present invention relates to compounds of the invention wherein n is 0, 1, or 2; m is 1; $R^1$ and $R^2$ are independently selected from hydrogen and —CH₃; $R^3$ is hydrogen; $R^4$ is at each instance independently selected from —F, —Cl, —Br, —CH₃, and —CN; or a pharmaceutically acceptable salt thereof.

A further preferred embodiment of the compounds of the present invention relates to compounds of the invention wherein m is 1; $R^1$ and $R^2$ are —CH₃; $R^3$ is —CN; n is 0 or 1; $R^4$ is —F, or a pharmaceutically acceptable salt thereof.

An especially preferred embodiment of compounds of the present invention is 4-(6,6-dimethyl-4,5-dihydro-1H-cyclopenta[c]pyrazol-4-yl)benzonitrile:

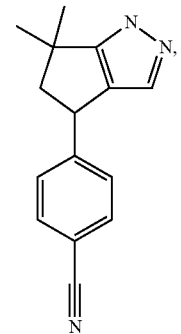 [SMILES: CC1(C)CC(c2ccc(C#N)cc2)c2cn[nH]c21]

or a pharmaceutically acceptable salt thereof.

Another especially preferred embodiment of compounds of the present invention is 4-[(4R)-(6,6-dimethyl-4,5-dihydro-1H-cyclopenta[c]pyrazol-4-yl)]benzonitrile:

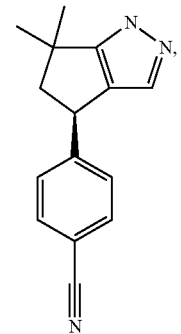 [SMILES: CC1(C)C[C@H](c2ccc(C#N)cc2)c2cn[nH]c21]

or a pharmaceutically acceptable salt thereof.

A further especially preferred compound of the present invention is 4-[(4R)-(6,6-dimethyl-4,5-dihydro-1H-cyclopenta[c]pyrazol-4-yl)]benzonitrile.

Another especially preferred compound of the present invention is 4-(6,6-dimethyl-4,5-dihydro-1H-cyclopenta[c]pyrazol-4-yl)-3-fluoro-benzonitrile:

or a pharmaceutically acceptable salt thereof.

A further especially preferred compound of the present invention is 4-(6,6-dimethyl-4,5-dihydro-1H-cyclopenta[c]pyrazol-4-yl)-3-fluoro-benzonitrile, Isomer 1, or a pharmaceutically acceptable salt thereof.

An additional especially preferred compound of the present invention is 4-(6,6-dimethyl-4,5-dihydro-1H-cyclopenta[c]pyrazol-4-yl)-3-fluoro-benzonitrile.

An even further especially preferred compound of the present invention is 4-(6,6-dimethyl-4,5-dihydro-1H-cyclopenta[c]pyrazol-4-yl)-3-fluoro-benzonitrile, Isomer 1.

The compounds of the invention are inhibitors of aldosterone synthase. Thus, the present invention provides a method of inhibiting aldosterone synthase that comprises administering to a patient in need of said treatment an aldosterone synthase-inhibiting amount of a compound of the present invention. It is preferred that the patient to be treated by the administration of the compounds of the present invention is a mammal, preferably human.

As inhibitors of aldosterone synthase, the compounds of the present invention are believed to be useful for the treatment of chronic kidney disease, diabetic neuropathy, congestive heart failure, and hypertension.

In a preferred embodiment, the present invention provides a method of treating chronic kidney disease comprising administering a compound of the invention to a patient in need thereof.

In another preferred embodiment, a compound of the present invention provides a method for treating diabetic nephropathy, said method comprising administering an effective amount of a compound of the invention or a pharmaceutically acceptable salt thereof to a patient in need thereof.

In yet another preferred embodiment the present invention provides a method for treating chronic kidney disease comprising co-administering a compound of the invention and an ACE inhibitor to a patient in need thereof.

In an additional preferred embodiment the present invention provides a method for treating chronic kidney diseases comprising co-administering a compound of the invention and an ARB to a patient in need thereof.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of the present invention, or salts thereof. The products of each step in the schemes below can be recovered by conventional methods, including extraction, evaporation, precipitation, chromatography, filtration, trituration, or crystallization.

Certain stereochemical centers have been left unspecified and certain substituents have been eliminated in the following schemes for the sake of clarity and are not intended to limit the teaching of the schemes in any way. Furthermore, individual isomers, enantiomers, or diastereomers may be separated at any convenient point in the synthesis of compounds of the present invention by methods such as chiral chromatography. Additionally, the intermediates described in the following schemes contain a number of nitrogen protecting groups. The variable protecting group may be the same or different in each occurrence depending on the particular reaction conditions and the particular transformations to be performed. The protection and deprotection conditions are well known to the skilled artisan and are described in the literature. See, e.g., Greene and Wuts, *Protective Groups in Organic Synthesis*, Third Edition, Chapter 7, John Wiley and Sons Inc., (1999).

The abbreviations used herein are defined according to *Aldrichimica Acta*, Vol. 17, No. 1, 1984. Other abbreviations are defined as follows: "ACN" refers to acetonitrile; "BINAP" refers to 2,2'-bis(diphenylphosphino)-1,1'-binaphthalene; "Bredereck's reagent" refers to tert-butoxy bis(dimethylamino)methane; "$Rh_2Cl_2(COD)_2$" refers to cyclooctadiene rhodium chloride dimer; "CMV" refers to cytomegalovirus; "DCM" refers to dichloromethane; "DMEA" refers to dimethylethylamine; "DMF" refers to dimethylformamide; "DMF-DMA" refers to dimethylformamide-dimethyl acetal or 1,1-dimethoxy-N,N-dimethylmethanamine; "DMEM" refers to Dulbecco's Modified Eagle's Medium; "DMSO" refers to dimethylsulfoxide; "DOC" refers to 11-deoxycorticosterone; "EtOAc" refers to ethyl acetate; "EtOH" refers to ethyl alcohol or ethanol; "Ex" refers to example; "FA" refers to formic acid; "flash chromatography" refers to purification over silica gel; "HEC" refers to hydroxy ethyl cellulose; "IS" refers to internal standard; "IPA" refers to isopropyl alcohol or isopropanol; "LiHMDS" refers to lithium bis(trimethylsilyl)amide; "MeOH" refers to methyl alcohol or methanol; "MTBE" refers to methyl t-butyl ether; "NMP" refers to N-methylpyrrolidone; "PdAllylCl" refers to π-Allylpalladium(II) chloride dimer; "$Pd_2(dba)_3$" refers to tris(dibenzylideneacetone)dipalladium; "Phosphine ligand" refers to di-tert-butyl(2',4',6'-triisopropylbiphenyl-2-yl)phosphine; "Prep" refers to preparation; "SFC" refers to supercritical fluid chromatography; "TFA" refers to trifluoroacetic acid; "THF" refers to tetrahydrofuran; "THP" refers to tetrahydropyranyl; "Tr" refers to retention time and "Tosyl" refers to toluenesulfonyl.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

Scheme I

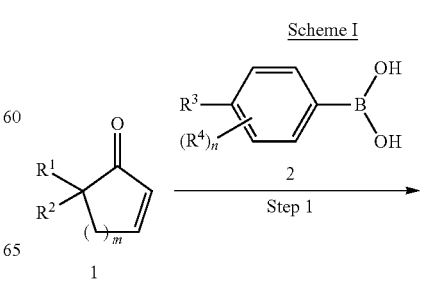

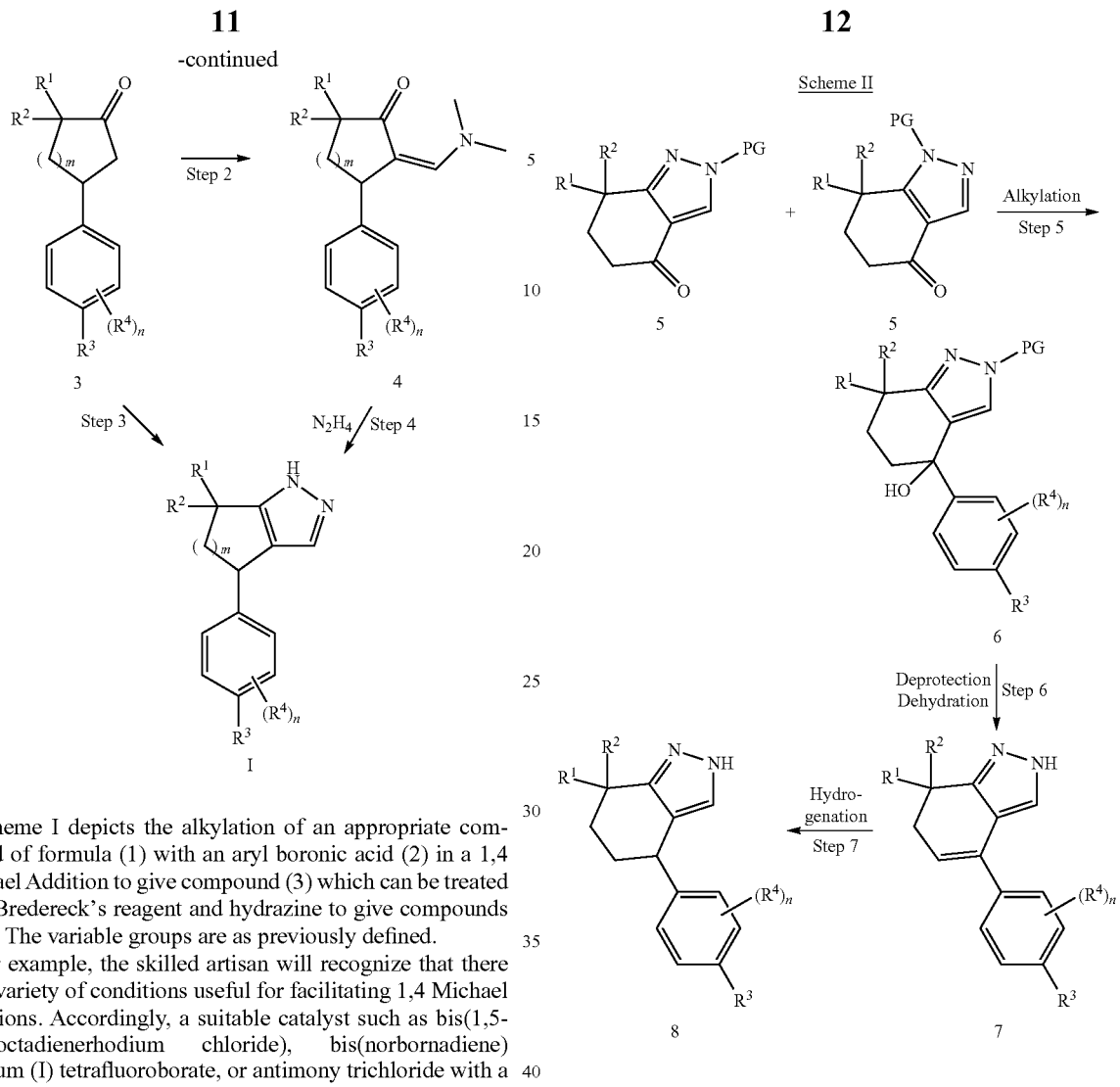

Scheme I depicts the alkylation of an appropriate compound of formula (1) with an aryl boronic acid (2) in a 1,4 Michael Addition to give compound (3) which can be treated with Bredereck's reagent and hydrazine to give compounds of (I). The variable groups are as previously defined.

For example, the skilled artisan will recognize that there are a variety of conditions useful for facilitating 1,4 Michael Additions. Accordingly, a suitable catalyst such as bis(1,5-cyclooctadienerhodium chloride), bis(norbornadiene)rhodium (I) tetrafluoroborate, or antimony trichloride with a palladium (II) catalyst such as palladium acetate can be used along with the appropriate aryl boronic acid (2). A suitable phosphine reagent such as racemic-2,2'-bis(diphenylphosphino)-1,1'-binaphthyl or the chiral binap (S)-(−)-2,2'-bis(diphenylphosphino)-1,1'-binaphthyl can be used to attempt a chiral addition. An appropriate inorganic base such as sodium acetate, potassium acetate, potassium carbonate, or an organic base such as triethylamine with an appropriate solvent such as THF with isopropyl alcohol, dioxane and water or an acid such as acetic acid can be used to facilitate the reaction to give a compound of formula (3, Step 1). The ketone can then be alkylated with dimethylformamide-dimethyl acetal or t-butoxy bis(dimethylamino)methane (Bredereck's reagent) to give the dimethylaminomethylene adduct, compound (4. Step 2) which can then be cyclized to form the pyrazole using hydrazine, hydrazine hydrate, or hydrazine hydrochloride to give compounds of the present invention in Step 4. Alternatively, a compound of formula (3) can be taken directly to compounds of the present invention without isolation of the intermediate compound (4) by reaction with Bredereck's reagent and then reaction in situ with the hydrazine reagent to give compounds of the present invention, Step 3.

Alternatively, when $R^1$ and $R^2$ are both hydrogen, a gem dialkyl functionality can be installed using an iodo-alkyl reagent in the presence of a base, such as lithium hexamethyldisilylazide.

Alternatively, the appropriately protected tetrahydroindazol-4-one as a mixture of regioisomers of pyrazole can be separated chromatographically or reacted as a mixture. The pyrazole protecting group can reside on either nitrogen atom and was arbitrarily assigned. One skilled in the art will recognize the position of the pyrazole protecting can be interchanged without affecting the outcome of the subsequent reactions shown. "PG" is a protecting group for the amino group. Such protecting groups are well known and appreciated in the art. Compound 5 can be alkylated with a Grignard reagent which is prepared by the treatment of the appropriately substituted 4-iodo phenyl analog with isopropylmagnesium chloride or bromide in an appropriate solvent such as THF to give the 5,6-dihydro-2H-indazol-4-ol (6, Step 5). In one embodiment, the carbinols (6) can be dehydrated and de-protected in a single transformation to give the alkene (7, Step 6) by treatment with an acid such as HCl or TFA in an alcoholic solvent such as methanol. Compound (7) can then be reduced by hydrogenation to give compound (8, Step 7). Alternatively, the sequence can be accomplished by step-wise by treatment of (6) with TFA in DCM, the resulting olefin reduced by hydrogenation using catalysts such as Pt(OH)₂ and de-protected with a base such as KOH in MeOH to give compound (8).

Scheme III

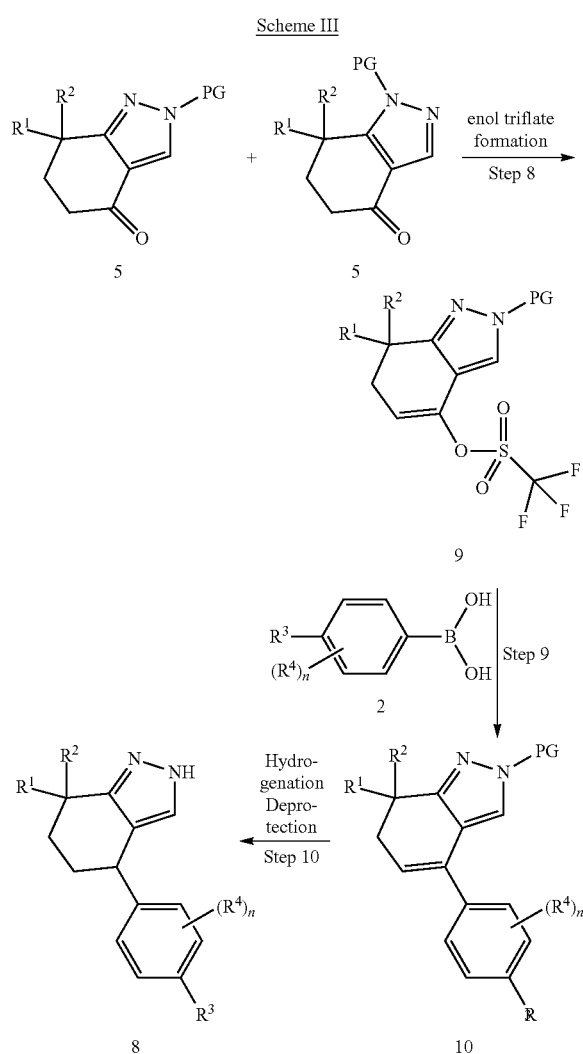

Scheme III depicts the alkylation of an appropriate compound of formula (9) with an aryl boronic acid to give compound (10) that after hydrogenation and deprotection gives a compound of the present invention. One skilled in the art can recognize the order of Step 10 can be transposed to give a compound of (8).

For example, the protected tetrahydroindazol-4-one regioisomers (5) can be separated chromatographically or reacted as a mixture with a suitable base such as LiHMDS in a polar aprotic solvent such as THF and the resulting enolate quenched with N-phenylbis(trifluoromethanesulfonamide) to give the enol triflate (9, Step 8) as a mixture of regioisomers that can be separated chromatographically or reacted as a mixture. Compound 9 can be reacted with an appropriate boronic acid (2) under Suzuki-Miyaura cross coupling conditions to give compound 10, Step 9. The skilled artisan will recognize that there are a variety of conditions useful for facilitating such cross-coupling reactions. Accordingly, a suitable palladium reagent includes tetrakis(triphenylphosphine)palladium(0), bis(triphenylphosphine)palladium(II) chloride, tris(dibenzylideneacetone)dipalladium (0) with tricyclohexylphosphine, (1,1'-bis(diphenylphosphino)ferrocene)palladium(II) chloride, or palladium(II) acetate. A suitable base includes cesium carbonate, sodium carbonate, potassium carbonate, or potassium phosphate tribasic monohydrate. Compound (10) can be hydrogenated and the resulting product de-protected to give a compound of Formula (I, Step 10). One skilled in the art can recognize that the final two transformations can be transposed to give a compound of (8).

PREPARATIONS AND EXAMPLES

The following preparations and examples further illustrate the invention.

Unless noted to the contrary, the compounds illustrated herein are named and numbered using Symyx® Draw version 3.2 (Symyx Solutions, Inc.) or IUPACNAME ACDLABS.

Preparation 1

5,5-Dimethylcyclopent-2-en-1-one 2,2-Dimethylcyclopentanone (50.0 g, 445.75 mmol) is added to a solution of allyl diethyl phosphate (165.4 g, 846.92 mmol) in t-amyl alcohol (557 mL). Potassium carbonate (75.5 g, 537.12 mmol), and Pd(OAc)$_2$ (5 g, 22.29 mmol) are added and the mixture is heated at 80° C. for 12 hours. The mixture is cooled to ambient temperature, diluted with acetone, (500 mL) filtered through diatomaceous earth, and concentrated to dryness. The crude material is distilled under vacuum (60° C. at 20 mm Hg) to give the title compound (30 g, 61%, 272.34 mmol). $^1$H NMR (300.13 MHz, CDCl$_3$) δ 7.62-7.59 (m, 1H), 6.12 (dt, J=5.9, 2.1 Hz, 1H), 2.54 (t, J=2.4 Hz, 2H), 1.10 (s, 6H).

Preparation 2

(4,5-Difluoro-2-methyl-phenyl)boronic acid n-Butyl lithium (4.6 mL, 11.5 mmol) is added to the mixture of 1-bromo-4,5-difluoro-2-methylbenzene (2.0 g, 9.6 mmol) and trimethyl borate (1.5 g, 14.5 mmol) in anhydrous tetrahydrofuran (30 mL), drop wise, at −78° C. over one hour, under an atmosphere of argon. The reaction mixture is stirred for another hour at the same temperature, quenched and acidified with 1 N HCl. The resulting mixture is extracted with ethyl acetate(3×). The combined organic layer is washed with brine, dried over anhydrous sodium sulfate, filtered, and concentrated in vacuo.

Preparation 3

(+/−)-4-(3,3-Dimethyl-4-oxo-cyclopentyl)benzonitrile

Bis(1,5-cyclooctadienerhodium chloride) (1.09 g, 2.18 mmol), racemic-2,2'-bis(diphenylphosphino)-1,1'-binaphthyl (3.05 g, 4.90 mmol) are added to tetrahydrofuran (72 mL) and the mixture is stirred under a nitrogen atmosphere for 30 minutes. This solution is added to a mixture of 4-cyanophenylboronic acid (80.04 g, 544.68 mmol), 5,5-dimethylcyclopent-2-en-1-one (24 g, 217.87 mmol), potassium carbonate (40.65 g, 294.13 mmol), tetrahydrofuran (144 mL), and isopropyl alcohol (16.7 mL) at 60° C. The mixture is stirred at 60° C. for 16 hours and then concentrated to dryness. The crude mixture is poured into water (500 mL) and is extracted with ethyl acetate (2×500 mL). The organic extracts are dried over MgSO$_4$, filtered through silica gel, and concentrated to dryness. The residue is purified by silica gel flash chromatography, eluting with 6:1 hexane:ethyl acetate to give the title compound (41 g, 88%, 192.24 mmol). $^1$H NMR (300.13 MHz, CDCl$_3$) δ 7.65-7.62 (m, 2H), 7.37 (d, J=8.1 Hz, 2H), 3.56-3.43 (m, 1H), 2.86-2.76 (m, 1H), 2.42-2.32 (m, 1H), 2.32-2.24 (m, 1H), 1.86 (t, J=12.4 Hz, 1H), 1.17 (s, 3H), 1.15 (s, 3H).

Preparation 4

(+/−)-3-(3,4-Difluorophenyl)cyclopentanone

To 3,4-difluorophenylboronic acid (9.47 g, 60 mmol), cyclopent-2-enone (4.93 g, 60 mmol), antimony trichloride (1.37 g, 6 mmol), sodium acetate, (9.84 g, 120 mmol) and palladium acetate (1.35 g, 6 mmol) are added to acetic acid (300 mL) under an argon atmosphere. The reaction is stirred at room temperature overnight. The reaction mixture is filtered and poured into water. The material is extracted with ethyl acetate (3×), washed with saturated sodium bicarbonate (3×), brine (3×), dried with sodium sulfate, filtered, and concentrated in vacuo. The material is purified using silica gel chromatography eluting with 10% ethyl acetate in pet ether to give the title compound as a yellow oil (6.9 g, 58%). $^1$H NMR (300 MHz, CDCl$_3$) δ 7.14-6.95 (m, 3H), 3.41-3.37 (m, 1H), 2.64-2.61 (m, 1H), 2.46-2.23 (m, 4H), 1.93-1.84 (m, 1H).

The following compounds are prepared essentially as described for (+/−)-3-(3,4-difluorophenyl)cyclopentanone.

TABLE 1

| Prep | Chemical Name | $^1$H NMR (300 MHz) δ or ES/MS |
|---|---|---|
| 5 | (+/−)-3-(4-Chloro-3-fluorophenyl)cyclopentanone | (CDCl$_3$) 7.32-7.37 (m, 1H), 7.05-6.96 (m, 2H), 3.41-3.38 (m, 1H), 2.72-2.60 (m, 1H), 2.46-2.25 (m, 4H), 1.93-1.85 (m, 1H). |
| 6 | (+/−)-3-(3,4-Dichlorophenyl)cyclopentanone | (m/z) 228 |
| 7 | (+/−)-2-Chloro-4-(3-oxocyclopentyl)benzonitrile | (m/z) 219 |
| 8 | (+/−)-3-(4-Trifluoromethylphenyl)cyclopentanone | (CDCl$_3$) 7.67 (d, J = 6.0 Hz, 2H), 7.55 (d, J = 9.0 Hz, 2H), 3.51-3.47 (m, 1H), 2.49-2.36 (m, 2H), 2.32-2.29 (m, 3H), 1.95-1.92 (m, 1H). |
| 9 | (+/−)-3-Chloro-4-(3,3-dimethyl-4-oxo-cyclopentyl)benzonitrile | 8.30-7.60 (m, 3H), 3.95-3.75 (m, 1H), 2.75-2.53 (m, 2H), 2.17 (ddd, J = 12.3, 6.1, 1.7 Hz, 1H), 1.84 (t, J = 12.1 Hz, 1H), 1.076 (s, 3H), 1.064 (s, 3H).$^d$ |
| 10 | (+/−)-4-(4,5-Difluoro-2-methyl-phenyl)-2,2-dimethyl-cyclopentanone | (m/z) 238 |
| 11 | (+/−)-2-Fluoro-4-(3,3-dimethyl-4-oxo-cyclopentyl)benzonitrile | 7.59-7.64 (m, 1H), 7.13-7.20 (m, 2H), 3.46-3.53 (m, 1H), 2.75-2.82 (m, 1H), 2.28-2.43 (m, 2H), 1.88-1.91 (m, 1H), 1.15-1.20 (m, 6H). |
| 12 | (+/−)-3-(4-Chlorophenyl)cyclopentanone | 7.28-7.31 (m, 2H), 7.16-7.20 (m, 2H), 3.36-3.39 (m, 1H), 2.61-2.69 (m, 1H), 2.23-2.48 (m, 4H), 1.93-2.03 (m, 1H). |
| 13 | (+/−)-4-(3-Oxocyclopentyl)benzonitrile | 7.64 (d, J = 8.4 Hz, 2H), 7.37 (d, J = 8.4 Hz, 2H), 3.54-3.42 (m, 1H), 2.74-2.66 (m, 1H), 2.54-2.43 (m, 2H), 2.37-2.27 (m, 2H), 2.02-1.91 (m, 1H). |
| 14 | (+/−)-3-(4-Fluorophenyl)cyclopentanone | 7.25-7.18 (m, 2H), 7.05-7.00 (t, 2H), 3.48-3.31 (m, 1H), 2.67 (dd, 1H), 2.51-2.22 (m, 4H), 2.02-1.85 (m, 1H). |
| 15 | (+/−)-4-(4-Chlorophenyl)-2,2-dimethyl-cyclopentanone | (m/z) 223 (M + 1) |
| 16 | (+/−)-4-(3-Chlorophenyl)-2,2-dimethyl-cyclopentanone | 7.28-7.2 (m, 3H), 7.1 (d, 1H), 3.48-3.37 (m, 1h), 2.73 (dd, 1H), 2.3 (dd, 1H), 2.25-2.19 (m, 1H), 1.8 (t, 1H), 1.15 (s, 3H), 1.1 (s, 3H) |
| 17 | (+/−)-4-(4-Chloro-3-fluorophenyl)-2,2-dimethyl-cyclopentanone | (m/z) 239.0 (M − 1) |
| 18 | (+/−)-4-(4-Chloro-2-fluorophenyl)-2,2-dimethyl-cyclopentanone | (m/z) 241.0 |
| 19 | (+/−)-4-(3-Bromo-5-fluorophenyl)-2,2-dimethyl-cyclopentanone | 7.19 (s, 1H), 7.10 (d, 1H), 6.86 (d, 1H), 3.4-3.3 (m, 1H), 2.74 (dd, 1H), 2.3 (dd, 1H), 2.25-2.19 (m, 1H), 1.8 (t, 1H), 1.11 (s, 3H), 1.05 (s, 3H). |
| 20 | (+/−)-4-(3,4-Difluorophenyl)-2,2-dimethyl-cyclopentanone | (m/z) 224.0 |
| 21 | (+/−)-4-(4-Fluorophenyl)-2,2-dimethyl-cyclopentanone | (m/z) 205.0 (M − 1) |
| 22 | (+/−)-4-(2-Chlorophenyl)-2,2-dimethyl-cyclopentanone | (m/z) 223.0 (M + 1) |
| 23 | (+/−)4-(3-Chloro-4-fluorophenyl)-2,2-dimethyl-cyclopentanone | 7.25 (d, 1H), 7.15-7.05 (m, 2H), 3.4-3.3 (m, 1H), 2.74 (dd, 1H), 2.3 (dd, 1H), 2.25-2.19 (m, 1H), 1.8 (t, 1H), 1.11 (s, 3H), 1.05 (s, 3H) |
| 24 | (+/−)-2,2-Dimethyl-4-phenyl-cyclopentanone | (m/z) 189.0 (M + 1) |
| 25 | (+/−)-3-(3,3-Dimethyl-4-oxocyclopentyl)benzonitrile | 7.51-7.39 (m, 4H), 3.5-3.39 (m, 1H), 2.78 (dd, 1H), 2.32 (dd, 1H), 2.29-2.2 (m, 1H), 1.81 (t, 1H), 1.14 (s, 3H), 1.1 (s, 3H) |

Preparation 26

(+/−)-(2Z)-3-(3,4-Difluorophenyl)-2-((dimethylamino)methylene)cyclopentanone

To (+/−)-3-(3,4-difluorophenyl)cyclopentanone (6.9 g, 35 mmol) is added N,N-dimethylformamide dimethylacetal (80 mL) and stirred at 80° C. overnight. The mixture is cooled to room temperature and concentrated in vacuo. The residue is purified by silica gel flash chromatography, eluting with 2% methanol in chloroform, to give the crude mixture as a yellow oil (8.5 g, 96%). LC/MS (M+H) 234.

The following compounds are prepared essentially as described for (+/−)-(2Z)-3-(3,4-difluorophenyl)-2-((dimethylamino)methylene)cyclopentanone.

TABLE 2

| Prep. | Chemical Name | ES/MS (m/z) (M + 1) |
|---|---|---|
| 27 | (+/−)-(2Z)-3-(4-Chloro-3-fluorophenyl)-2-((dimethylamino)methylene)cyclopentanone | 268 |
| 28 | (+/−)-(2Z)-3-(3,4-Dichlorophenyl)-2-((dimethylamino)methylene)cyclopentanone[a] | 284 |
| 29 | (+/−)-2-Chloro-4-[(2Z)-2-(dimethylamino-methylene)-3-oxo-cyclopentyl]benzonitrile[b] | 275 |
| 30 | (+/−)-(2Z)-3-(4-Trifluoromethylphenyl)-2-((dimethylamino)methylene)cyclopentanone | |
| 31 | (+/−)-3-Chloro-4-[(2Z)-2-(dimethylamino-methylene)-4,4-dimethyl-3-oxo-cyclopentyl]benzo-nitrile | 303 |
| 32 | (+/−)-(5Z)-4-(4,5-Difluoro-2-methyl-phenyl)-5-(dimethylaminomethylene)-2,2-dimethyl-cyclo-pentanone | |
| 33 | (+/−)-2-Fluoro-4-[(2Z)-2-(dimethylamino-methylene)-4,4-dimethyl-3-oxo-cyclopentyl]benzo-nitrile | 287 |
| 34 | (+/−)-(2Z)-3-(4-Chlorophenyl)-2-((dimethyl-amino)methylene)cyclopentanone[c] | 250 |
| 35 | (+/−)-4-[(2Z)-2-(Dimethylamino-methylene)-3-oxo-cyclopentyl]benzonitrile | 241 |
| 36 | (+/−)-(2Z)-3-(4-Fluorophenyl)-2-((dimethyl-amino)methylene)cyclopentanone | 234 |
| 37 | (+/−)-4-[(2Z)-2-(dimethylaminomethylene)-4,4-dimethyl-3-oxo-cyclopentyl]benzonitrile[a] | 269 |

[a]After the reaction is concentrated in vacuo, the residue is diluted with ethyl acetate and water. The organic phase is separated and the aqueous is extracted three times with ethyl acetate. The organic layers are combined and washed with brine, dried over sodium sulfate, and concentrated in vacuo. Flash chromatography eluting with 50% ethyl acetate and pet ether, followed by 2% methanol/dichloromethane gives the title compound.
[b]Same work up as in (a). Flash chromatography eluting with 50% ethyl acetate and pet ether, followed by 4% methanol/dichloromethane gives the title compound.
[c]The reaction is carried out with butoxy-N,N,N',N'-tetramethylmethanediamine in toluene and heated to 60° C., overnight. The work up is described in (a) and the chromatography utilizes 2% methanol/dichloromethane.

Preparation 38

(+/−)-4-[(2Z)-2-(Dimethylaminomethylene)-4,4-diethyl-3-oxo-cyclopentyl]benzonitrile Lithium hexamethyldisilylazide (40 mL, 40 mmol) is added to a solution of (+/−)-4-[(2Z)-2-(dimethylaminomethylene)-3-oxo-cyclopentyl]benzonitrile (0.96 g, 4 mmol) in anhydrous tetrahydrofuran (100 mL), drop wise at −30° C., under an argon atmosphere, and stirred for one hour. At the same temperature, iodoethane (12.48 g, 80 mmol) is added to the mixture drop wise, and the reaction mixture is allowed to warm to room temperature and stirred overnight. The reaction is quenched by adding saturated ammonium chloride (100 mL). The resulting mixture is extracted with ethyl acetate (3×100 mL). The combined organic layer is dried over anhydrous sodium sulfate and concentrated in vacuo to give the crude product as a black solid (0.99 g, 83.4%). This is used in the next step without further purification. ES/MS (m/z) 297 (M+1).

The following compound is prepared essentially as described for (+/−)-4-[(2Z)-2-(dimethylaminomethylene)-4,4-diethyl-3-oxo-cyclopentyl]benzonitrile.

TABLE 3

| Prep. | Chemical Name | ES/MS (m/z) (M + 1) |
|---|---|---|
| 39 | (+/−)-4-[(2Z)-2-(Dimethylaminomethylene)-4-methyl-3-oxo-cyclopentyl]benzonitrile | 255 |

Preparation 40

(3S)-3-(3-Chlorophenyl)cyclopentanone

Bis(norbornadiene)rhodium(I)tetrafluoroborate (0.20 g, 0.53 mmol) and (S)-(−)-2,2'-Bis(diphenylphosphino)-1,1'-binaphthyl (0.30 g, 0.48 mmol) are dissolved 1,4-dioxane (18 mL). The solution is degassed with nitrogen for 2 hours. 3-Chlorophenylboronic acid (4.95 g, 31.67 mmol) is dissolved in dioxane (24 mL) and water (6 mL). The mixture is degassed for another 2 hours. The two solutions are combined and stirred for two hours under a nitrogen stream. 2-Cyclopentenone (2.0 g, 24.36 mmol) and triethylamine (2.1 mL, 15.07 mmol) are added to the reaction sequentially, via syringe. This is stirred until completion under a stream of nitrogen. The reaction is filtered through a pad of diatomaceous earth and concentrated in vacuo. The residue is purified via silica gel flash chromatography, eluting with 20% ethyl acetate in hexane to give the title compound (4.23 g, 89.2%) as a clear, yellow oil. $^1$H NMR (400 MHz, CDCl$_3$) δ 1.9 (1H, M), 2.25 (2H, M), 2.45 (2H, M), 2.65 (1H, M), 3.35 (1H, M), 7.1 (1H, D), 7.25 (3H, M).

The following compounds are prepared essentially as described for (3S)-3-(3-chlorophenyl)cyclopentanone.

TABLE 4

| Prep. | Chemical Name | $^1$H NMR (400 MHz, CDCl$_3$) δ or MS |
|---|---|---|
| 41 | (3S)-3-Phenyl-cyclopentanone | 1.95 (1H, M), 2.25 (2H, M), 2.45 (2H, M), 2.65 (1H, M), 3.40 (1H, M), 7.20 (3H, M), 7.3 (2H, T) |
| 42 | (3S)-3-(3-Fluoro-phenyl)cyclopentanone | 1.9 (1H, M), 2.25 (2H, M), 2.4 (2H, M), 2.6 (1H, M), 3.4 (1H, M), 6.9 (2H, M), 7.0 (1H, D), 7.25 (1H, M) |
| 43 | (3S)-3-[4-Fluoro-3-(trifluoromethyl)cyclopentanone | 1.9 (1H, M), 2.3 (2H, M), 2.45 (2H, M), 2.65 (1H, M), 3.4 (1H, M), 7.1 (1H, T), 7.4 (2H, M) |
| 44 | 2-Fluoro-4-[(1S)-3-oxocyclo-pentyl]benzonitrile | ES/MS (m/z) 202 (M − 1) |

Preparation 45

4-(4-Chloro-2-fluoro-phenyl)-2,2-dimethyl-cyclopentanone

A solution of 5,5-dimethylcyclopent-2-en-1-one (42.0 g, 343.15 mmol), 4-chloro-2-fluorophenylboronic acid (94.47 g, 514.72 mmol), sodium acetate (56.30 g, 686.30 mmol), acetic acid (1130 mL), Pd(OAc)$_2$ (7.70 g, 34.31 mmol), and antimony trichloride (7.83 g, 34.31 mmol) are stirred at ambient temperature for 16 hours. The solvent is evaporated to low volume and the residual acetic acid is removed using toluene. MTBE (500 mL) is added and the resulting precipitate is filtered off and discarded. The MTBE solution is washed with water (500 mL), aq. NaHCO$_3$ (2×300 mL), dried over MgSO$_4$, filtered, and concentrated to dryness. The residue is purified by silica gel flash chromatography, eluting with hexane to hexane 10% MTBE to give the title compound (72 g, 87%). $^1$H NMR (300.16 MHz, CDCl$_3$) δ 7.21-7.06 (m, 3H), 3.67-3.59 (m, 1H), 2.81-2.72 (m, 1H), 2.41-2.31 (m, 1H), 2.21 (ddd, J=12.6, 6.3, 2.2 Hz, 1H), 1.89 (t, J=12.3 Hz, 1H), 1.159 (s, 3H), 1.137 (s, 3H).

Preparation 46

4-(3,3-Dimethyl-4-oxo-cyclopentyl)-3-fluoro-benzonitrile

Di-tert-butyl(2',4',6'-triisopropylbiphenyl-2-yl)phosphine (1.75 g, 4.11 mmol) is added to a solution of 4-(4-chloro-2-fluoro-phenyl)-2,2-dimethyl-cyclopentanone (33 g, 137.10 mmol), zinc cyanide (9.66 g, 82.26 mmol), and N-methylpyrrolidone (148.50 mL) at 125° C. and the mixture is stirred for 15 minutes. π-Allylpalladium(II) chloride dimer (0.76 g, 4.11 mmol) is added to the solution and the mixture is stirred for 30 minutes. Diatomaceous earth (15 g) is added and the mixture is cooled to rt. The mixture is filtered through diatomaceous earth and washed with MTBE (450 mL). Water (450 mL) is added and the mixture is extracted with MTBE (150 mL). The mixture is washed with brine, dried over $MgSO_4$, filtered, and concentrated to dryness to give the title compound (34 g, 97%). $^1$H NMR (300.16 MHz, $CDCl_3$) δ 7.47-7.33 (m, 3H), 3.76-3.63 (m, 1H), 2.83-2.76 (m, 1H), 2.43-2.33 (m, 1H), 2.25 (dd, J=6.3, 12.6 Hz, 1H), 1.91 (t, J=12.3 Hz, 1H), 1.168 (s, 3H), 1.147 (s, 3H).

Preparation 47

1-(p-Tolylsulfonyl)-6,7-dihydro-5H-indazol-4-one and 2-(p-Tolylsulfonyl)-6,7-dihydro-5H-indazol-4-one 2,5,6,7-Tetrahydro-indazol-4-one (12.8 g, 91.2 mmol) is added to dichloromethane (500 mL) and triethylamine (25.4 mL, 182.4 mmol). p-Toluenesulfonyl chloride (17.74 g, 91.2 mmol) is then added and the mixture is stirred for 16 hours at room temperature. The pH of the dark solution is adjusted to pH 3 with 1.0 N HCl, and the mixture is transferred to a separatory funnel. The organics are washed with water, brine, dried over sodium sulfate, filtered, and evaporated to dryness. The residue is purified by silica gel chromatography eluting with 1:1 hexanes/ethyl acetate to give the title compounds (9.0 g, 34%) as a 1.5:1 ratio of regioisomers. ES/MS m/z 291 (M+H).

Preparation 48

4-[4-Hydroxy-1-(p-tolylsulfonyl)-6,7-dihydro-5H-indazol-4-yl]benzonitrile and 4-[4-Hydroxy-2-(p-tolylsulfonyl)-6,7-dihydro-5H-indazol-4-yl]benzonitrile 4-Iodobenzonitrile (6.21 g, 26.84 mmol) is added to THF (40.0 mL) and cooled to 0° C. Isopropylmagnesium chloride (16.11 mL, 32.1 mmol) is added and stirred at 0° C. under nitrogen atmosphere for 60 minutes. A 1.5:1 mixture of 1-(p-tolylsulfonyl)-6,7-dihydro-5H-indazol-4-one and 2-(p-tolylsulfonyl)-6,7-dihydro-5H-indazol-4-one (6.24 g, 21.5 mmol) is dissolved in THF, and this solution is added to the anion drop-wise at 0° C. and then allowed to warm to room temperature. The tan solution is quenched with HCl (3.0 mL, 1 N) and concentrated to dryness. The residue is purified by silica gel chromatography eluting with 60% hexanes/ethyl acetate to give the title compounds. This reaction is run a second time at the same scale and products of both runs combined to give the title compounds as a mixture of regioisomers (8.98 g, 53%). ES/MS m/z 394 (M+H).

The following compounds are prepared essentially by the method of 4-[4-hydroxy-1-(p-tolylsulfonyl)-6,7-dihydro-5H-indazol-4-yl]benzonitrile and 4-[4-hydroxy-2-(p-tolylsulfonyl)-6,7-dihydro-5H-indazol-4-yl]benzonitrile using the appropriate aryl halide.

TABLE 5

| Prep. | Aryl Halide | Chemical Name | ES/MS (m/z) (M + 1) |
|---|---|---|---|
| 49 | 4-Tolylmagnesium Bromide (2.0 eq) | 4-(p-Tolyl)-1-(p-tolylsulfonyl)-6,7-dihydro-5H-indazol-4-ol and 4-(p-Tolyl)-2-(p-tolylsulfonyl)-6,7-dihydro-5H-indazol-4-ol | 383, 364 (M − 18) |
| 50 | p-Iodo anisole (2.0 eq) | 4-(4-Methoxyphenyl)-2-(p-tolylsulfonyl)-6,7-dihydro-5H-indazol-4-ol and 4-(4-methoxyphenyl)-1-(p-tolylsulfonyl)-6,7-dihydro-5H-indazol-4-ol | 399, 381 (M − 18) |
| 51 | 4-Chlorophenyl-mangnesium Bromide (2.0 eq) | 4-(4-Chlorophenyl)-1-(p-tolylsulfonyl)-6,7-dihydro-5H-indazol-4-ol And 4-(4-chlorophenyl)-2-(p-tolylsulfonyl)-6,7-dihydro-5H-indazol-4-ol | 405, 404 |

Preparation 52

4-(6,7-Dihydro-2H-indazol-4-yl)benzonitrile

A mixture of 4-[4-hydroxy-1-(p-tolylsulfonyl)-6,7-dihydro-5H-indazol-4-yl]benzonitrile and 4-[4-hydroxy-2-(p-tolylsulfonyl)-6,7-dihydro-5H-indazol-4-yl]benzonitrile (8.56 g, 21.7 mmol) is added to 4.0 M HCl in dioxane (20.0 mL, 80.0 mmol), heated to 80° C. for 2.0 h and concentrated to dryness. The residue is dissolved in dichloromethane/water, separated and the organics are dried over $Na_2SO_4$, filtered, and evaporated. The residue is purified by silica gel chromatography 80% ethyl acetate/hexanes to give the title compound (3.21 g, 67%). ES/MS m/z 222 (M+H), 220 (M−H).

The following compounds are prepared essentially by the method of 4-(6,7-dihydro-2H-indazol-4-yl)benzonitrile.

TABLE 6

| Prep. | Chemical Name | ES/MS (m/z) (M + 1) |
|---|---|---|
| 53 | 4-(p-Tolyl)-6,7-dihydro-1H-indazole | 211 |
| 54 | 4-(4-Methoxyphenyl)-6,7-dihydro-1H-indazole | 227 |

Preparation 55

4-(4-Chlorophenyl)-2-(p-tolylsulfonyl)-6,7-dihydroindazole 4-(4-Chlorophenyl)-2-(p-tolylsulfonyl)-6,7-dihydro-5H-indazol-4-ol (0.76 g, 1.89 mmol) is added to dichloromethane (20.0 mL), triethylsilane (6.04 mL, 37.7 mmol), and TFA (0.16 mL, 2.07 mmol) and stirred at room temperature for 2.0 h. The reaction is quenched with saturated $NaHCO_3$, separated, the organics washed with brine dried over $Na_2SO_4$, filtered, and evaporated to dryness to give the title compound (0.622 g, 86%). $^1$H NMR ($CDCl_3$) δ 2.42 (s, 3H), 2.55 (m, 2H), 2.82 (t, 2H), 5.98 (t, 1H), 7.37-7.31 (m, 6H), 7.81 (s, 1H), 7.87 (d, 2H).

Preparation 56

4-(4-Chlorophenyl)-2-(p-tolylsulfonyl)-4,5,6,7-tetrahydroindazole 4-(4-Chlorophenyl)-2-(p-tolylsulfonyl)-6,7-dihydroindazole (0.62 g, 1.89 mmol) is added to ethanol (20.0 mL) and ethyl acetate (10 mL). Platinum (IV) oxide (0.22 g) is added and the reaction is stirred under 40 psi of hydrogen at room temperature for 6.0 h. The mixture is filtered through a plug of diatomaceous earth and evaporated under reduced pressure to give the title compound (0.503 g, 80%). LC/MS m/z 389 (M+H), Tr=2.704 min.

Preparation 57

1-Tetrahydropyran-2-yl-6,7-dihydro-5H-indazol-4-one and 2-Tetrahydropyran-2-yl-6,7-dihydro-5H-indazol-4-one 2,5,6,7-Tetrahydro-indazol-4-one (US2009/11180 A1) (5.0 g, 36.7 mmol) is added to a solution of dihydropyran (3.4 g, 40.4 mmol) in $CH_2Cl_2$ (100 mL) and the mixture is treated with p-toluensulfonic acid (0.1 g, 0.58 mmol) and stirred at room temperature for 3 days. Saturated $NaHCO_3$ solution is added, and the contents are transferred to a separatory funnel. The organics are washed with brine, dried over $Na_2SO_4$, filtered and concentrated to dryness. The residue is purified by silica gel chromatography eluting with $CH_2Cl_2$ to give the title compounds (5.32 g, 66%) as a mixture of regioisomers. $^1$H NMR (300 MHz, CDCl$_3$) δ 8.04 (s, 1H), 7.90 (s, 1H), 5.35-5.32 (m, 1H), 4.11-4.01 (m, 1H), 3.73-3.66 (m, 1H), 2.96-2.91 (m, 1H), 2.87-2.84 (m, 1H), 2.51-2.47 (m, 2H), 2.19-2.02 (m, 4H), 1.72-1.61 (m, 4H).

Preparation 58

(1-Tetrahydropyran-2-yl-6,7-dihydroindazol-4-yl)trifluoromethanesulfonate and (2-Tetrahydropyran-2-yl-6,7-dihydroindazol-4-yl)trifluoromethanesulfonate 1-Tetrahydropyran-2-yl-6,7-dihydro-5H-indazol-4-one and 2-tetrahydropyran-2-yl-6,7-dihydro-5H-indazol-4-one (2.03 g, 9.22 mmol) are added to THF (100 mL), the solution is cooled to −78° C., and treated with LiHMDS (10.14 mL, 10.14 mmol). After stirring for 1 hour, a solution of N-phenylbis(trifluouromethanesulfonimide) (3.68 g, 10.14 mmol) in THF (20 mL) is added drop wise at −78° C., and allowed to warm to room temperature over 17 hours. The reaction is quenched with saturated $NH_4Cl$, diluted with diethyl ether, and the organics are washed with 0.1 N HCl, brine, dried over $Na_2SO_4$, filtered, and concentrated to dryness. The residue is purified by silica gel chromatography eluting with 85:15 hexanes/ethyl acetate to give the title compounds (2.3 g, 51%) as a 3:1 mixture of regioisomers. ES/MS m/z 352 (M+H), 269 (M-THP).

Preparation 59

3-Methyl-4-(1-tetrahydropyran-2-yl-6,7-dihydroindazol-4-yl)benzonitrile or 3-Methyl-4-(2-tetrahydropyran-2-yl-6,7-dihydroindazol-4-yl)benzonitrile (1-Tetrahydropyran-2-yl-6,7-dihydroindazol-4-yl)trifluoromethanesulfonate, (2-tetrahydropyran-2-yl-6,7-dihydroindazol-4-yl)trifluoromethanesulfonate (1.0 g, 2.84 mmol) and (4-cyano-2-methylphenyl)boronic acid (0.502 g, 3.12 mmol) are added to dioxane (80.0 mL) and $Na_2CO_3$ (0.601 mg, 5.68 mmol, 2.0 M) and de-gassed with a stream of nitrogen. The solution is treated with tetrakis(triphenylphosphine)palladium (0.33 g, 0.28 mmol) and heated to 80° C. under nitrogen for 17 hours. The mixture is cooled to ambient temperature and filtered through a plug of diatomaceous earth. The filtrate is diluted with ethyl acetate and the layers are separated. The organics are washed with saturated $NaHCO_3$, brine, dried over $Na_2SO_4$, filtered, and concentrated to dryness. The residue is purified by silica gel chromatography eluting with 9:1 hexanes/ethyl acetate to 4:1 hexanes/ethyl acetate to give one of the title compounds (0.492 g, 55%) as a single regioisomer. ES/MS m/z 320 (M+H), 236 (M-THP).

The following compound is prepared essentially by the method of 3-methyl-4-(1-tetrahydropyran-2-yl-6,7-dihydroindazol-4-yl)benzonitrile or 3-methyl-4-(2-tetrahydropyran-2-yl-6,7-dihydroindazol-4-yl)benzonitrile using the appropriate boronic acid.

TABLE 7

| Prep | Boronic Acid | Chemical Name | ES/MS (m/z) (M + 1) |
|---|---|---|---|
| 60 | (4-Cyano-3-methoxyphenyl)boronic acid | 2-Methoxy-4-(1-tetrahydropyran-2-yl-6,7-dihydroindazol-4-yl)benzonitrile or 2-Methoxy-4-(2-tetrahydropyran-2-yl-6,7-dihydroindazol-4-yl)benzonitrile | 336 |

Preparation 61

3-Methyl-4-(1-tetrahydropyran-2-yl-4,5,6,7-tetrahydroindazol-4-yl)benzonitrile or 3-Methyl-4-(2-tetrahydropyran-2-yl-4,5,6,7-tetrahydroindazol-4-yl)benzonitrile 3-Methyl-4-(1-tetrahydropyran-2-yl-6,7-dihydroindazol-4-yl)benzonitrile or 3-methyl-4-(2-tetrahydropyran-2-yl-6,7-dihydroindazol-4-yl)benzonitrile (0.492 g, 1.54 mmol) and 5% Pd/C wt/wt % (0.15 g) is added to EtOH (20.0 mL) and the mixture is stirred under 45-35 psi of hydrogen for 72 hours. The mixture is filtered through a plug of diatomaceous earth and concentrated to dryness. The residue is purified by silica gel chromatography eluting with 7:3 hexanes/ethyl acetate to give one of the title compounds (0.162 g, 33%) as a single regioisomer. ES/MS m/z 322 (M+H).

The following compound is prepared essentially by the method of 3-methyl-4-(1-tetrahydropyran-2-yl-4,5,6,7-tetrahydroindazol-4-yl)benzonitrile or 3-methyl-4-(2-tetrahydropyran-2-yl-4,5,6,7-tetrahydroindazol-4-yl)benzonitrile.

TABLE 8

| Prep | Chemical Name | ES/MS (m/z) (M + 1) |
|---|---|---|
| 62 | 2-Methoxy-4-(1-tetrahydropyran-2-yl-4,5,6,7-tetrahydroindazol-4-yl)benzonitrile or 2-Methoxy-4-(2-tetrahydropyran-2-yl-4,5,6,7-tetrahydroindazol-4-yl)benzonitrile | 338 |

Preparation 63

2-Fluoro-4-(1-tetrahydropyran-2-yl-6,7-dihydroindazol-4-yl)benzonitrile and 2-Fluoro-4-(2-tetrahydropyran-2-yl-6,7-dihydroindazol-4-yl)benzonitrile (1-Tetrahydropyran-2-yl-6,7-dihydroindazol-4-yl)trifluoromethanesulfonate, (2-tetrahydropyran-2-yl-6,7-dihydroindazol-4-yl)trifluoromethanesulfonate (0.201 g, 0.57 mmol) and (4-cyano-3-fluorophenyl)boronic acid (0.103 g, 0.63 mmol) are added to dioxane (7.0 mL) and $Na_2CO_3$ (0.12 mg, 1.14 mmol, 2.0 M), and the mixture is degassed with a stream of nitrogen. The solution is treated with tetrakis(triphenylphosphine)palladium (0.07 g, 0.06 mmol) and heated to 80° C. under nitrogen for 6 hours, and an additional 72 hours at room temperature. The reaction is quenched with water, diluted with ethyl acetate, the organic layer is separated, washed with saturated $NaHCO_3$, brine, dried over $Na_2SO_4$, filtered, and concentrated to dryness. The residue, is taken on to the next reaction without additional purification (0.231 g, 125%).

Preparation 64

4-(6,7-Dihydro-1H-indazol-4-yl)-2-fluoro-benzonitrile

2-Fluoro-4-(1-tetrahydropyran-2-yl-6,7-dihydroindazol-4-yl)benzonitrile and 2-fluoro-4-(2-tetrahydropyran-2-yl-6,7-dihydroindazol-4-yl)benzonitrile (0.23 g, 0.71 mmol) and $H_2SO_4$ (0.08 mL, 1.43 mmol) are added to $CH_3CN$ (5.0 mL) and the solution is stirred at room temperature for 6.0 hours. Aqueous $Na_2CO_3$ is added to basify the reaction, which is then diluted with ethyl acetate, the layers separated, and the aqueous back extracted with ethyl acetate (3×). The organics are combined, dried over $Na_2SO_4$, filtered, and concentrated to dryness. The residue is purified by silica gel flash chromatography eluting with 99:1 $CH_2Cl_2$/MeOH to give the title compound (0.102 g, 60%). ES/MS m/z 240 (M+H).

Preparation 65

(+/−)-(trans)-4-(4-Methyl-3-oxo-cyclohexyl)benzonitrile and

Preparation 66

(+/−)-(cis)-4-(4-Methyl-3-oxo-cyclohexyl)benzonitrile

Bis(1,5-cyclooctadienerhodium chloride) (0.06 g, 0.12 mmol), racemic-2,2'-bis(diphenylphosphino)-1,1'-binaphthyl (0.18 g, 0.29 mmol) are added to tetrahydrofuran (40 mL) and the mixture is stirred under a nitrogen atmosphere for 30 minutes. This solution is added to a mixture of 4-cyanophenylboronic acid (2.31 g, 15.69 mmol), 6-methylcyclohex-2-en-1-one (Journal of Organic Chemistry, 1980 45(10), 1852-1863) (1.28 g, 11.62 mmol), potassium carbonate (2.19 g, 15.69 mmol), and isopropyl alcohol (1.1 mL) at 60° C. The mixture is stirred at 60° C. for 16 hours and then concentrated to dryness. The crude mixture is poured into water (10 mL) and is extracted with ethyl acetate (2×20 mL). The organic extracts are dried over $MgSO_4$, filtered through silica gel, and concentrated to dryness. The residue is purified by silica gel flash chromatography, eluting with 20% EtOAc/hexane to give (trans)-4-(4-methyl-3-oxo-cyclohexyl)benzonitrile (0.55 g, 22%) as the first eluting isomer and (cis)-4-(4-methyl-3-oxo-cyclohexyl)benzonitrile (0.55 g, 22%) as the second eluting isomer. ES/MS m/z 214 (M+H).

Preparation 67

(+/−)-(cis/trans)-4-[7-Methyl-4,5,6,7-tetrahydro-2H-indazol-4-yl]benzonitrile (cis)-4-(4-Methyl-3-oxo-cyclohexyl)benzonitrile (0.55 g, 2.58 mmol) is added to toluene (10.0 mL) and tert-butoxybis(dimtheylamino)methane (0.67 mL, 3.22 mmol) and stirred at 120° C. for 16 hours. The mixture is cooled to room temperature and concentrated in vacuo. The residue is added to MeOH (10.0 mL) and hydrazine (0.07 mL, 2.32 mmol) and stirred at 80° C. for 1.0 hour. The mixture is cooled to room temperature and concentrated in vacuo. The residue is purified by silica gel chromatography (35%-55% EtOAc/hexanes) to give (+/−)-(cis/trans)-4-[7-methyl-4,5,6,7-tetrahydro-2H-indazol-4-yl]benzonitrile (0.360 g, 58%). ES/MS m/z 238 (M+H).

Preparation 68

(+/−)-4-(4,4-Dimethyl-3-oxo-cyclohexyl)-3-methyl-benzonitrile

4-Cyano-2-methylphenylboronic acid (0.81 g, 5 mmol), 6,6-dimethylcyclohex-2-enone (Canadian Journal of Chemistry, 1981, 59, 2096-2115) (0.55 g, 5 mmol), $SbCl_3$ (0.11 g, 0.5 mmol), sodium acetate (0.82 g, 10 mmol), and palladium acetate (0.11 g, 0.5 mmol) are added to acetic acid (30 mL) under an atmosphere of argon. The reaction mixture is stirred at room temperature for three days. The mixture is filtered and the filtrate is poured into water (150 mL). The organic phase is separated and the aqueous phase is extracted with ethyl acetate (3×100 mL). The combined organic layers are washed with saturated sodium bicarbonate solution (3×100 mL), brine (3×50 mL), dried over anhydrous sodium sulfate, and concentrated in vacuo. The residue is purified by silica gel column chromatography eluting with pet ether: EtOAc=10:1 to give the title compound as a light yellow solid (0.6 g, 50%). GC/MS 241 (M+1).

The following compounds are prepared essentially by the method of (+/−)-4-(4,4-dimethyl-3-oxo-cyclohexyl)-3-methyl-benzonitrile.

TABLE 9

| Prep | Chemical Name | GC/MS (m/z) (M + 1) |
|---|---|---|
| 69 | (+/−)-4-(4,4-Dimethyl-3-oxo-cyclohexyl)-3-fluoro-benzonitrile | 245 |
| 70 | (+/−)-4-(4,4-Dimethyl-3-oxo-cyclohexyl)-2-fluoro-benzonitrile | a | a. $^1$H NMR (300 MHz, $CDCl_3$) δ 7.60-7.56 (m, 1H), 7.14-7.07 (m, 2H), 3.08-3.00 (m, 1H), 2.73-2.67 (m, 1H), 2.51-2.46 (m, 1H), 2.03-1.60 (m, 4H), 1.25 (s, 3H), 1.12 (s, 3H).

Preparation 71

(+/−)-4-(4-Methoxyphenyl)-4,5,6,7-tetrahydro-1H-indazole 4-(4-Methoxyphenyl)-6,7-dihydro-1H-indazole (0.141 g, 0.62 mmol) is dissolved in EtOH (10 mL) and THF (4 mL) and 5% Pd/C (0.090 g) is added. The mixture is stirred under hydrogen (40 psi) for 4 hrs. The mixture is filtered through diatomaceous earth and the filtrate is evaporated to dryness. The residue is purified by silica gel chromatography eluting with 98:2 CH$_2$Cl$_2$:MeOH to give the title compound (0.121 g, 85%). ES/MS m/z 229 (M+1).

Example 1

4-[(4R)-(6,6-Dimethyl-4,5-dihydro-1H-cyclopenta[c]pyrazol-4-yl)]benzonitrile

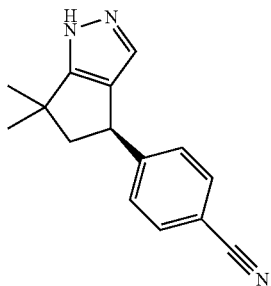 [SMILES: CC1(C)C[C@H](c2ccc(C#N)cc2)c2cn[nH]c21]

DMF-DMA (46.26 g, 388.22 mmol) is added to (+/−) 4-(3,3-dimethyl-4-oxo-cyclopentyl)benzonitrile (46 g, 213.52 mmol) and the mixture is stirred at 100° C. for 16 hours. Excess DMF-DMA is removed by vacuum. Isopropyl alcohol (248 mL) is added followed by hydrazine monohydrate (10.69 g, 324.61 mmol) and acetic acid (11.12 mL). The mixture is heated at 80° C. for 12 hours. The mixture is cooled to ambient temperature and the solvent is evaporated to dryness. Water (50 mL) is added and the mixture is extracted with DCM (3×50 mL). The organic extracts are dried over MgSO$_4$, filtered, and concentrated to dryness. The residue is purified by silica gel flash chromatography, eluting with 1:1 hexane-ethyl acetate. The mixture of enantiomers is purified by chiral HPLC Chiralpak AD using 40% IPA/60% n-hexane (2% DMEA), column size, 20 nm, 8×25 cm, flow rate of 300 mL/min, UV detection 254 nm, and loading of 5 g/5 min. The R enantiomer (isomer 1) is obtained by collecting the fraction eluting at 5.53 minutes.

The R enantiomer is further purified by silica gel flash chromatography eluting with 4:1 hexane-acetone to give the title compound (9.2 g, 38.77 mmol) as a yellow solid. ES/MS (m/z) 238(M+1), $^1$H NMR (300.16 MHz, CDCl$_3$) δ 7.60-7.58 (m, 2H), 7.36 (d, J=8.2 Hz, 2H), 7.17 (s, 1H), 4.36 (t, J=8.0 Hz, 1H), 2.74 (dd, J=7.7, 12.6 Hz, 1H), 2.23-2.16 (m, 1H), 1.40 (s, 3H), 1.35 (s, 3H).

Example 1a

4-[(4R)-6,6-dimethyl-4,5-dihydro-1H-cyclopenta[c]pyrazol-4-yl]benzonitrile hemihydrate

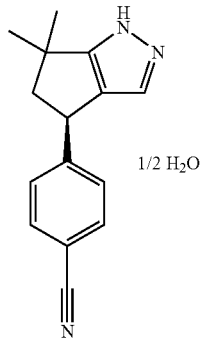 [SMILES: CC1(C)C[C@H](c2ccc(C#N)cc2)c2cn[nH]c21]

Suspend 4-[(4R)-(6,6-Dimethyl-4,5-dihydro-1H-cyclopenta[c]pyrazol-4-yl)]benzonitrile (45 mg, 0.190 mmol) in water (1 mL) and slurry at ambient temperature for 1 hour. The solids are vacuum filtered and air dried to give the title compound (35 mg, 76%).

X-Ray Powder Diffraction

The XRD patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The U.S. Pharmacopeia 33—National Formulary 28 Chapter <941> Characterization of Crystalline Solids by X-ray Powder Diffraction (XRPD) Official Oct. 1, 2010-Feb. 1, 2011. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.85 and 26.77 degrees 2-theta.

A prepared sample of the title compound is characterized by an XRD pattern using CuKa radiation as having diffraction peaks (2-theta values) as described in Table 1 below. Specifically the pattern contains a peak at 23.75 in combination with one or more of the peaks selected from the group consisting of 12.19, 15.53, 17.23, 17.78 and 20.61 with a tolerance for the diffraction angles of 0.2 degrees.

| Peak | Angle (2-Theta °) | Intensity (%) |
|---|---|---|
| 1 | 6.06 | 25 |
| 2 | 12.19 | 65 |
| 3 | 15.53 | 71 |
| 4 | 15.77 | 33 |
| 5 | 17.23 | 58 |
| 6 | 17.78 | 95 |
| 7 | 18.31 | 20 |
| 8 | 19.00 | 24 |
| 9 | 20.61 | 98 |
| 10 | 21.62 | 26 |
| 11 | 22.31 | 45 |
| 12 | 23.75 | 100 |
| 13 | 24.55 | 19 |
| 14 | 25.01 | 21 |
| 15 | 26.09 | 27 |
| 16 | 26.41 | 44 |
| 17 | 27.96 | 43 |

Example 1b

4-[(4R)-6,6-Dimethyl-4,5-dihydro-1H-cyclopenta[c]pyrazol-4-yl]benzonitrile; phosphoric acid

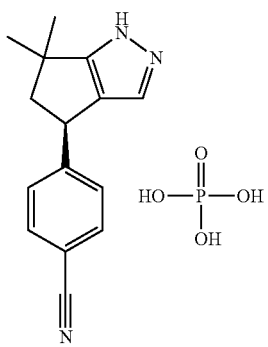

Dissolve 4-[(4R)-(6,6-dimethyl-4,5-dihydro-1H-cyclopenta[c]pyrazol-4-yl)]benzonitrile (445 mg) in isopropyl acetate (1 mL). To this mixture, is added 15 M phosphoric acid (150 µL, 1.2 eq) drop wise. Localized rapid crystallization is noted and brief sonication in a water bath precipitated a large plug of bright white solids. This plug is broken up by adding isopropyl acetate (3 mL) to give a loose slurry. The solids are then vacuum filtered and air dried to give the title compound (585 mg, 93%).

X-Ray Powder Diffraction

The XRD patterns of crystalline solids are prepared as described in Example 1a.

The title compound is characterized by an XRD pattern using CuKa radiation as having diffraction peaks (2-theta values) as described in Table 1 below. Specifically the pattern contains a peak at 5.56 in combination with one or more of the peaks selected from the group consisting of 12.69, 16.97, 18.25, 19.39 and 22.92 with a tolerance for the diffraction angles of 0.2 degrees.

| Peak | Angle (2-Theta °) | Intensity (%) |
|---|---|---|
| 1 | 5.564 | 100 |
| 2 | 11.016 | 5 |
| 3 | 12.685 | 8 |
| 4 | 14.711 | 3 |
| 5 | 16.967 | 23 |
| 6 | 18.248 | 10 |
| 7 | 18.900 | 4 |
| 8 | 19.390 | 16 |
| 9 | 21.291 | 6 |
| 10 | 22.920 | 13 |
| 11 | 24.539 | 7 |
| 12 | 24.772 | 7 |
| 13 | 25.041 | 5 |

Example 2

4-[(4S)-6,6-dimethyl-4,5-dihydro-1H-cyclopenta[c]pyrazol-4-yl]benzonitrile

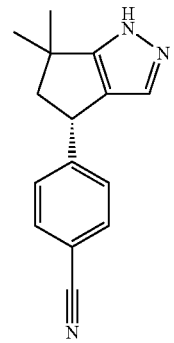 [SMILES: CC1(C)C[C@@H](c2ccc(C#N)cc2)c2cn[nH]c21]

Example 2 is prepared essentially by the method described for Example 1 by collecting the fraction eluting at 10.25 min. The collected fraction is further purified by silica gel chromatography with 80% hexane and 20% acetone to give the title compound (2 g).

Example 3

(+/−)-4-(4-Chlorophenyl)-6,6-dimethyl-4,5-dihydro-1H-cyclopenta[c]pyrazole (+/−)-4-(4-Chlorophenyl)-2,2-dimethyl-cyclopentanone (0.250 g, 1.12 mmol) is dissolved in isopropanol (5 mL) and stirred. tert-Butoxybis(dimethylamino)methane (0.33 mL, 1.57 mmol) is added drop wise to the reaction. The reaction is heated in a sealed vial at 100° C. for 12 hours, cooled to room temperature, and concentrated to dryness. The residue is diluted with isopropanol (5 mL). Hydrazine hydrate (0.11 mL, 2.25 mmol) is added to the reaction and heated to 100° C. in a sealed vial for 5 hours. The reaction is concentrated in vacuo. The residue is purified by silica gel flash chromatography eluting with 20% ethyl acetate in hexanes to obtain the title compound (0.035 g, 13%) as a yellow film. ES/MS (m/z) 247.0 (M+1).

The following Examples are prepared essentially as described for (+/−)-4-(4-Chlorophenyl)-6,6-dimethyl-4,5-dihydro-1H-cyclopenta[c]pyrazole.

TABLE 10

| Ex No. | Chemical Name | Structure | ES/MS (m/z) (M + H) |
|---|---|---|---|
| 4 | (+/−)-4-(3-Chlorophenyl)-6,6-dimethyl-1,4,5,6-tetrahydrocyclopenta[c]pyrazole | 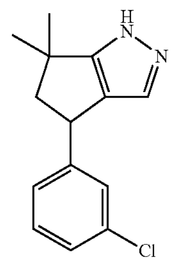 [SMILES: CC1(C)CC(c2cccc(Cl)c2)c2cn[nH]c21] | 247 |
| 5 | (+/−)-4-(4-Chloro-3-fluorophenyl)-6,6-dimethyl-1,4,5,6-tetrahydrocyclopenta[c]pyrazole | 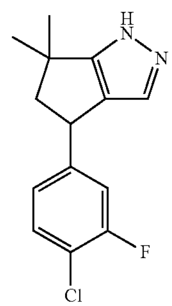 [SMILES: CC1(C)CC(c2ccc(Cl)c(F)c2)c2cn[nH]c21] | 265 |
| 6 | (+/−)-4-(4-Chloro-2-fluorophenyl)-6,6-dimethyl-1,4,5,6-tetrahydrocyclopenta[c]pyrazole | 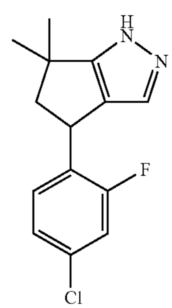 [SMILES: CC1(C)CC(c2ccc(Cl)cc2F)c2cn[nH]c21] | 265 |
| 7 | (+/−)-4-(3-Bromo-5-fluoro-phenyl)-6,6-dimethyl-1,4,5,6-tetrahydrocyclopenta[c]pyrazole | 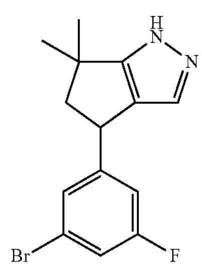 [SMILES: CC1(C)CC(c2cc(F)cc(Br)c2)c2cn[nH]c21] | 309 |
| 8 | (+/−)-4-(3,4-Difluorophenyl)-6,6-dimethyl-1,4,5,6-tetrahydrocyclopenta[c]pyrazole | 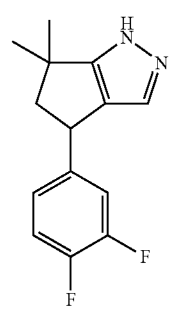 [SMILES: CC1(C)CC(c2ccc(F)c(F)c2)c2cn[nH]c21] | 249 |

TABLE 10-continued

| Ex No. | Chemical Name | Structure | ES/MS (m/z) (M + H) |
|---|---|---|---|
| 9 | (+/−)-4-(4-Fluorophenyl)-6,6-dimethyl-1,4,5,6-tetrahydrocyclopenta[c]pyrazole | 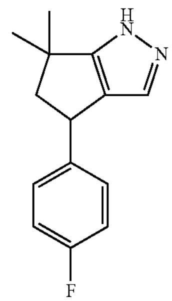 [SMILES: CC1(C)CC(c2ccc(F)cc2)c2cn[nH]c21] | 231 |
| 10 | (+/−)-4-(2-Chlorophenyl)-6,6-dimethyl-1,4,5,6-tetrahydrocyclopenta[c]pyrazole | 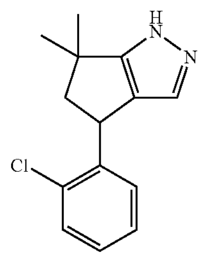 [SMILES: CC1(C)CC(c2ccccc2Cl)c2cn[nH]c21] | 247 |
| 11 | (+/−)-4-(3-Chloro-4-fluoro-phenyl)-2,2-dimethyl-1,4,5,6-tetrahydrocyclopenta[c]pyrazole | 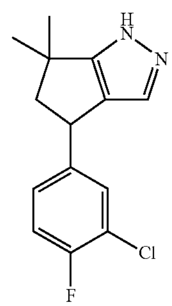 [SMILES: CC1(C)CC(c2ccc(F)c(Cl)c2)c2cn[nH]c21] | 265 |
| 12 | (+/−)-6,6-Dimethyl-1,4,5,6-tetrahydrocyclopenta[c]pyrazole | 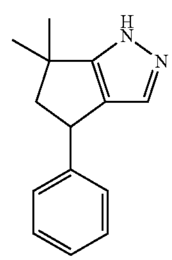 [SMILES: CC1(C)CC(c2ccccc2)c2cn[nH]c21] | 213 |
| 13 | (+/−)-3-(6,6-Dimethyl-1,4,5,6-tetrahydrocyclopenta[c]pyrazole)benzonitrile | 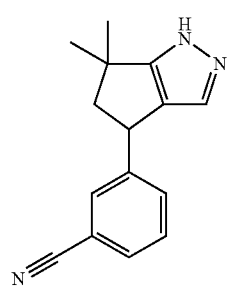 [SMILES: CC1(C)CC(c2cccc(C#N)c2)c2cn[nH]c21] | 238 |

Example 14

(+/−)-4-(3,4-Difluorophenyl)-1,4,5,6-tetrahydrocyclopenta[c]pyrazole

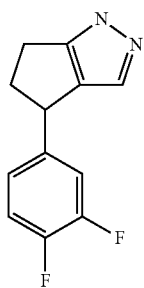 [SMILES: Fc1ccc(C2CCc3[nH]ncc32)cc1F]

To the mixture of (+/−)-(2Z)-3-(3,4-difluorophenyl)-2-((dimethylamino)methylene)cyclopentanone (8.5 g, 34 mmol) in ethanol (200 mL), is added hydrazine hydrate (15 mL) and the mixture is heated to 80° C., overnight. The mixture is cooled to room temperature and concentrated in vacuo. The residue is purified by preparative HPLC using a CXTH instrument with a DAISO 10 μC18 250×50 mm column, a 9 mL injection, a flow rate of 70 mL/min, a wavelength of 214 nm and a mobile phase of 10-80% acetonitrile in 0.1% TFA/H$_2$O to give the title compound as a white solid (2.1 g, 28%). ES/MS m/z 221 (M+H).

The following Examples are prepared essentially as described for (+/−)-4-(3,4-difluorophenyl)-1,4,5,6-tetrahydrocyclopenta[c]pyrazole.

TABLE 11

| Ex No. | Chemical Name | Structure | ES/MS (m/z) (M + 1) |
|---|---|---|---|
| 15 | (+/−)-4-(4-Chloro-3-fluorophenyl)-1,4,5,6-tetrahydrocyclopenta[c]pyrazole | | 237 |
| 16 | (+/−)-4-(3,4-Dichlorophenyl)-1,4,5,6-tetrahydrocyclopenta[c]pyrazole hydrochloride[a] | | 254 |
| 17 | (+/−)-2-Chloro-4-(1,4,5,6-tetrahydrocyclopenta[c]pyrazol-4-yl)benzonitrile hydrochloride[a] | 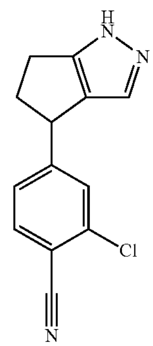 | 244 |
| 18 | (+/−)-4-(4-Trifluoromethylphenyl)-1,4,5,6-tetrahydrocyclopenta[c]pyrazole | 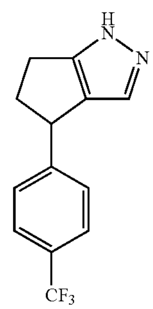 [SMILES: FC(F)(F)c1ccc(C2CCc3[nH]ncc32)cc1] | 253 |
| 19 | (+/−)-3-Chloro-4-(6,6-dimethyl-1,4,5,6-tetrahydrocyclopenta[c]pyrazol-4-yl)benzonitrile[b] | 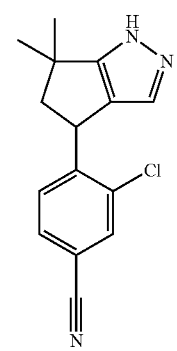 [SMILES: CC1(C)CC(c2ccc(C#N)cc2Cl)c2cn[nH]c21] | 272 |
| 20 | (+/−)-4-(4,5-Difluoro-2-methylphenyl)-6,6-dimethyl-1,4,5,6-tetrahydrocyclopenta[c]pyrazole[c] | 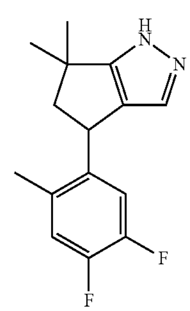 [SMILES: Cc1cc(F)c(F)cc1C1CC(C)(C)c2[nH]ncc21] | 263 |

TABLE 11-continued

| Ex No. | Chemical Name | Structure | ES/MS (m/z) (M + 1) |
|---|---|---|---|
| 21 | (+/−)-4-(6,6-Diethyl-1,4,5,6-tetrahydrocyclopenta[c]pyrazol-4-yl)benzonitrile hydrochloride[a,c] | 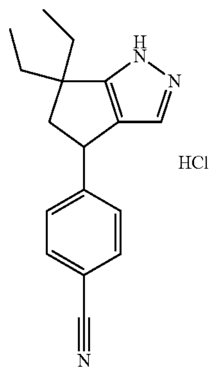 [SMILES: CCC1(CC)CC(c2ccc(C#N)cc2)c2cn[nH]c21 ; Cl] | 266 |
| 22 | (+/−)-4-(6-Methyl-1,4,5,6-tetrahydrocyclopenta[c]pyrazol-4-yl)benzonitrile hydrochloride[a,c] | 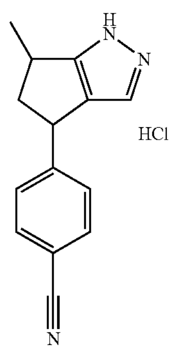 [SMILES: CC1CC(c2ccc(C#N)cc2)c2cn[nH]c21 ; Cl] | 224 |
| 23 | (+/−)-2-Fluoro-4-(6,6-dimethyl-1,4,5,6-tetrahydrocyclopenta[c]pyrazol-4-yl)benzonitrile hydrochloride[a] | 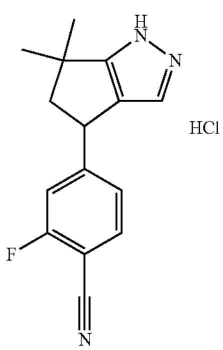 [SMILES: CC1(C)CC(c2ccc(C#N)c(F)c2)c2cn[nH]c21 ; Cl] | 256 |
| 24 | (+/−)-4-(4-Chlorophenyl)-1,4,5,6-tetrahydrocyclopenta[c]pyrazole | 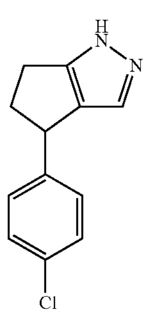 [SMILES: Clc1ccc(C2CCc3[nH]ncc32)cc1] | 219 |
| 25 | (+/−)-4-(1,4,5,6-Tetrahydrocyclopenta[c]pyrazol-4-yl)benzonitrile | 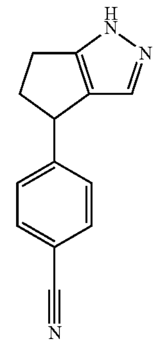 [SMILES: N#Cc1ccc(C2CCc3[nH]ncc32)cc1] | 210.2 |
| 26 | (+/−)-4-(4-Fluorophenyl)-1,4,5,6-tetrahydrocyclopenta[c]pyrazole[c] | 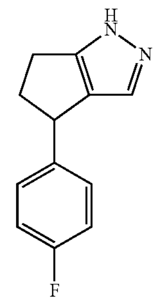 [SMILES: Fc1ccc(C2CCc3[nH]ncc32)cc1] | 203.2 |

[a]Upon completion and concentration in vacuo, the residue is diluted with saturated sodium bicarbonate solution and extracted with ethyl acetate (3×). The organics are combined, washed with brine, dried over sodium sulfate, and concentrated in vacuo. This is purified with silica gel chromatography, eluting with 2:1 pet ether:ethyl acetate. The crude product is then subjected to the above mentioned prep HPLC conditions, and acidified with HCl in ethyl acetate, to give a white solid as the title compound.
[b]A catalytic amount of acetic acid is used. The reaction is run at room temperature for twelve hours.
[c]Hydrazine hydrochloride is used instead of hydrazine hydrate.

Example 27

4-(3,4-Difluorophenyl)-1,4,5,6-tetrahydrocyclopenta[c]pyrazole, isomer 1

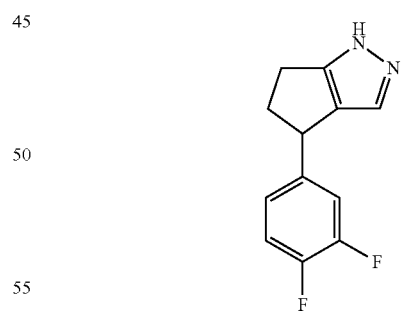

The racemic material is subjected to chiral chromatography using Chiralcel® OJ-H 4.6×150 mm column with 20% 3A EtOH:80% CO$_2$, a flow rate of 5.0 mL/min at UV of 230 nm to give the pure enantiomer, isomer 1. This is then re-purified with silica gel chromatography eluting with a step gradient, from 25%-50% ethyl acetate/toluene, to give the title compound (0.121 g, 6.1%). ES/MS (m/z) 221.2 (M+1).

The following Examples are prepared essentially as described for 4-(3,4-difluorophenyl)-1,4,5,6-tetrahydrocyclopenta[c]pyrazole isomer 1.

TABLE 12

| Ex No. | Chemical Name | Structure | ES/MS (m/z) (M + 1) |
|---|---|---|---|
| 28 | 4-(4-Fluorophenyl)-1,4,5,6-tetrahydrocyclopenta[c]pyrazole, isomer 1[a] | 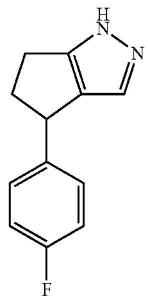 [SMILES: Fc1ccc(C2CCc3[nH]ncc32)cc1] | 203.2 |
| 29 | 4-(4-Chloro-3-fluorophenyl)-1,4,5,6-tetrahydrocyclopenta[c]pyrazole isomer 1[b] | 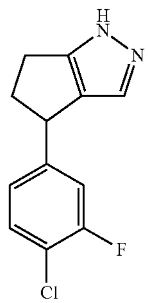 [SMILES: Fc1cc(C2CCc3[nH]ncc32)ccc1Cl] | 237.2 |
| 30 | 4-(3,4-Chloro-3-flurophenyl)-1,4,5,6-tetrahydrocyclopenta[c]pyrazole isomer 2[b] | 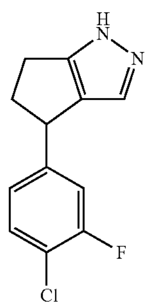 [SMILES: Fc1cc(C2CCc3[nH]ncc32)ccc1Cl] | 237.2 |
| 31 | 2-Fluoro-4-(6,6-dimethyl-1,4,5,6-tetrahydrocyclopenta[c]pyrazol-4-yl)benzonitrile, isomer 1[c] | 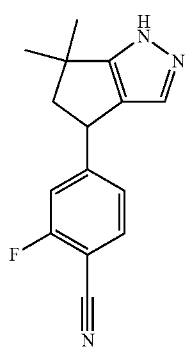 [SMILES: CC1(C)CC(c2ccc(C#N)c(F)c2)c2cn[nH]c21] | 256 |
| 32 | 4-(4-Chlorophenyl)-1,4,5,6-tetrahydrocyclopenta[c]pyrazole, isomer 1[d] | 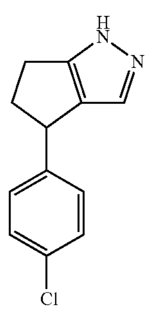 [SMILES: Clc1ccc(C2CCc3[nH]ncc32)cc1] | 219 |

TABLE 12-continued

| Ex No. | Chemical Name | Structure | ES/MS (m/z) (M + 1) |
|---|---|---|---|
| 33 | 4-(1,4,5,6-Tetrahydrocyclopenta[c]pyrazol-4-yl)benzonitrile, isomer 1[e] | 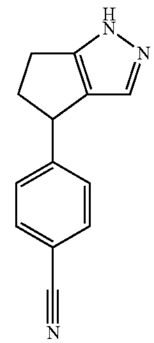 [SMILES: N#Cc1ccc(C2CCc3[nH]ncc32)cc1] | 210 |
| 34 | 4-(4-Chlorophenyl)-6,6-dimethyl-4,5-dihydro-1H-cyclopenta[c]pyrazole, isomer 1[f] | 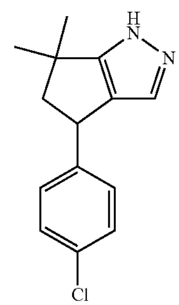 [SMILES: CC1(C)CC(c2ccc(Cl)cc2)c2cn[nH]c21] | 247 |
| 35 | 4-(3-Chlorophyenyl)-6,6-dimethyl-1,4,5,6-tetrahydrocyclopenta[c]pyrazole, isomer 1[g] | 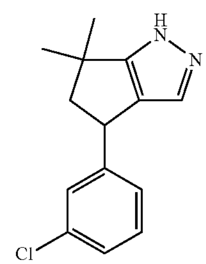 [SMILES: CC1(C)CC(c2cccc(Cl)c2)c2cn[nH]c21] | 247 |
| 36 | 4-(4-Chloro-3-fluorophenyl)-6,6-dimethyl-1,4,5,6-tetrahydrocyclopenta[c]pyrazole, isomer 1[h] | 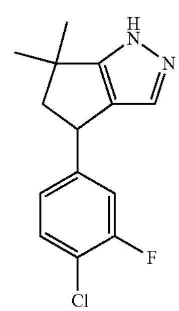 [SMILES: CC1(C)CC(c2ccc(Cl)c(F)c2)c2cn[nH]c21] | 265 |
| 37 | 4-(4-Chloro-2-fluorophenyl)-6,6-dimethyl-1,4,5,6-tetrahydrocyclopenta[c]pyrazole, isomer 1[i] | 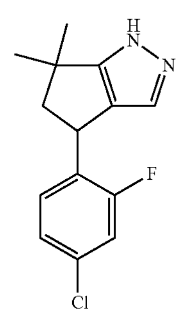 [SMILES: CC1(C)CC(c2ccc(Cl)cc2F)c2cn[nH]c21] | 265 |

TABLE 12-continued

| Ex No. | Chemical Name | Structure | ES/MS (m/z) (M+1) |
|---|---|---|---|
| 38 | 4-(4-Chloro-2-fluorophenyl)-6,6-dimethyl-1,4,5,6-tetrahydrocyclopenta[c]pyrazole, isomer 2[i] | 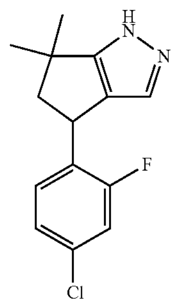 [SMILES: CC1(C)CC(c2ccc(Cl)cc2F)c2cn[nH]c21] | 265 |
| 39 | 4-(4-Fluorophenyl)-6,6-dimethyl-1,4,5,6-tetrahydrocyclopenta[c]pyrazole, isomer 1[k] | 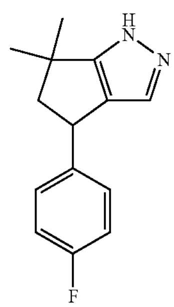 [SMILES: CC1(C)CC(c2ccc(F)cc2)c2cn[nH]c21] | 231 |
| 40 | 4-(2-Chlorophenyl)-6,6-dimethyl-1,4,5,6-tetrahydrocyclopenta[c]pyrazole, isomer 2[l] | 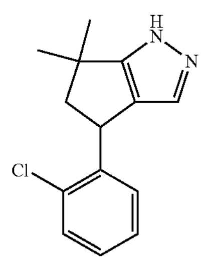 [SMILES: CC1(C)CC(c2ccccc2Cl)c2cn[nH]c21] | 247 |
| 41 | 4-Phenyl-6,6-dimethyl-1,4,5,6-tetrahydrocyclopenta[c]pyrazole, isomer 1[m] | 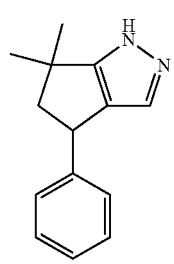 [SMILES: CC1(C)CC(c2ccccc2)c2cn[nH]c21] | 213 |
| 42 | 3-(6,6-Dimethyl-1,4,5,6-tetrahydrocyclopenta[c]pyrazole)benzonitrile isomer 1[n] | 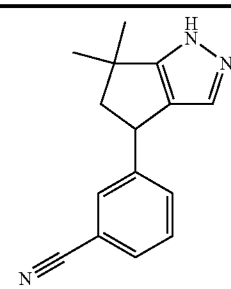 | 238 |

[a] Chiralcel® OJ-H column, 20% MeOH/CO2, 5 mL/min, 225 nM.
[b] Chiralcel® OJ-H column, 20% IPA(0.2% isopropyl amine/CO2, 5 mL/min, 225 nM
[c] Chiralpak® AD-H column, 0.2% DMEA/methanol, 30 mL/min, 225 nM.
[d] Chiracel® OJ-H column, 20% EtOH/CO2, 5 mL/min, 225 nM.
[e] Chiralpak® IC column, 30% IPA/CO2, 5 mL/min, 230 nM. After chiral chromatography, the product is chromatographed in a step gradient with 1-3% MeOH/chloroform, a 2nd chromatography with 2% MeOH/chloroform and crystallized with ether to give the final product.
[f] Chiralpak® AD-H column, 100% MeOH, 30 mL/min, 225 nM.
[g] Chiralpak® AD-H column, 100% MeOH, 30 mL/min, 225 nM.
[h] Chiralpak® AD-H column, 15% MeOH/$CO_2$, 70 mL/min, 225 nM.
[i] Chiralpak® OD-H column, 10% MeOH/CO2, 70 mL/min, 225 nM.
[k] Chiralpak® AD-H column, 100% ethanol, 18 mL/min, 225 nM.
[l] Chiralpak® AD-H column, 20% IPA/CO2, 70 mL/min, 225 nM.
[m] Chiralpak® AD-H column, 20% ethanol/CO2, 70 mL/min, 225 nM.
[n] Chiralpak® AD-H column, 4/1 ethanol/ACN, 25 mL/min, 225 nM.

Example 43

(4R)-4-(3-Chlorophenyl)-1,4,5,6-tetrahydrocyclopenta[c]pyrazole

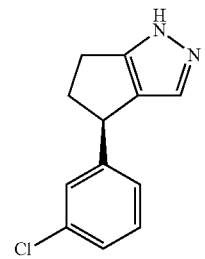 [SMILES: Clc1cccc([C@H]2CCc3[nH]ncc32)c1]

(3S)-3-(3-Chlorophenyl)cyclopentanone (1.5 g, 7.71 mmol) is dissolved in isopropanol (20 mL) and stirred. tert-Butoxybis(dimethylamino)methane (1.91 mL, 9.25 mmol) is added drop wise to the reaction. The reaction is heated to 125° C. for 12 hours. It is then cooled to room temperature and concentrated to dryness. The residue is diluted with isopropanol (20 mL). Hydrazine hydrate (0.37 mL, 11.56 mmol) is added to the reaction and the reaction is heated to 100° C. for 5 hours. The reaction is concentrated in vacuo and the residue is purified via silica gel chromatography, eluting with 20% ethyl acetate in hexanes to obtain the title product (1.099 g) as a yellow film. This material is further purified via chiral chromatography, employing a Chiralpak AD-H column, eluting with 20% methanol/$CO_2$, a flow rate of 70 mL/min, and UV detection at 225 nM. The title compound (0.442 g, 26.2%) is isolated as a clear oil. ES/MS (m/z) 219.0 (M+1).

The following Examples are prepared essentially as described for (4R)-4-(3-chlorophenyl)-1,4,5,6-tetrahydrocyclopenta[c]pyrazole.

TABLE 13

| Ex. No. | Chemical name | Structure | ES/MS (m/z) (M + H) |
|---|---|---|---|
| 44 | (4R)-4-Phenyl-1,4,5,6-tetrahydrocyclopenta[c]pyrazole | 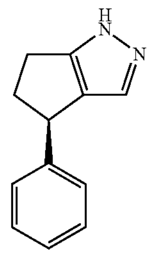 [SMILES: c1ccc([C@H]2CCc3[nH]ncc32)cc1] | 185.0 |
| 45 | (4R)-4-[3-Fluoro-4-(trifluoromethyl)phenyl]-1,4,5,6-tetrahydrocyclopenta[c]pyrazole | 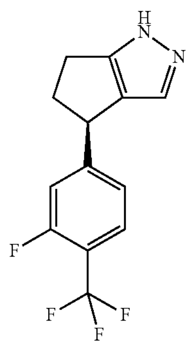 [SMILES: Fc1cc([C@H]2CCc3[nH]ncc32)ccc1C(F)(F)F] | 271.0 |
| 46 | (4R)-4-(3-Fluorophenyl)-1,4,5,6,-tetrahydrocyclopenta[c]pyrazole | 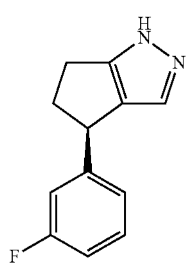 [SMILES: Fc1cccc([C@H]2CCc3[nH]ncc32)c1] | 203.0 |
| 47 | 2-Fluoro-4-[(4R)-1,4,5,6,-tetrahydrocyclopenta[c]pyrazol-4-yl]benzonitrile[a] | 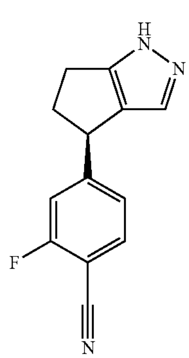 [SMILES: N#Cc1ccc([C@H]2CCc3[nH]ncc32)cc1F] | 228.0 |

[a]Chiralpak AD-H column, 100% MeOH, 30 mL/min, 225 nM.

Example 48

(+/−)-4-(6,6-Dimethyl-4,5-dihydro-1H-cyclopenta[c]pyrazol-4-yl)-3-fluoro-benzonitrile

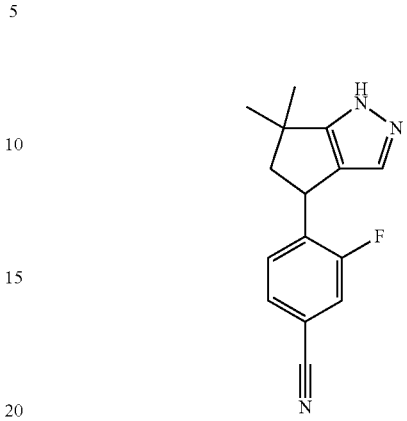

Methanamine, 1,1-dimethoxy-N,N-dimethyl-(42.05 g, 352.84 mmol) is added to 4-(3,3-dimethyl-4-oxo-cyclopentyl)-3-fluoro-benzonitrile (34 g, 117.61 mmol) and the mixture is stirred at 90° C. for 16 hours. The mixture is cooled to ambient temperature and the excess DMF-DMA is evaporated to dryness. To the crude residue is added: isopropyl alcohol (163.20 mL), hydrazine monohydrate (11.78 g, 235.22 mmol), and acetic acid (20.22 mL, 352.84 mmol) and the mixture is stirred at 70° C. for 2 hours. The mixture is cooled to ambient temperature and the solvent evaporated to dryness. The mixture is poured into water (200 mL) and is extracted with MTBE (2×200 mL). The mixture is washed with brine, dried over MgSO$_4$, filtered, and concentrated to dryness. The residue is purified by silica gel flash chromatography, eluting with hexane and 10% IPA to give the title compound (30 g, 99%). ES/MS (m/z) 256 (M+1), $^1$H NMR (300.16 MHz, DMSO) δ 12.62-12.60 (m, 1H), 7.82 (dd, J=1.5, 10.2 Hz, 1H), 7.62 (dd, J=1.5, 8.1 Hz, 1H), 7.42-7.34 (m, 1H), 4.52 (t, J=7.7 Hz, 1H), 2.73 (d, J=1.8 Hz, 1H), 2.07 (dd, J=8.1, 11.7 Hz, 1H), 1.25 (s, 6H).

Example 49

4-(6,6-Dimethyl-4,5-dihydro-1H-cyclopenta[c]pyrazol-4-yl)-3-fluoro-benzonitrile, isomer 1

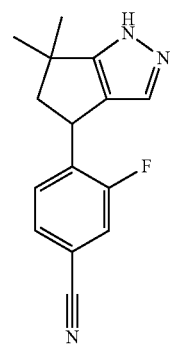 [SMILES: CC1(C)CC(c2ccc(C#N)cc2F)c2cn[nH]c21]

Racemic 4-(6,6-dimethyl-4,5-dihydro-1H-cyclopenta[c]pyrazol-4-yl)-3-fluoro-benzonitrile (14.4 g, 56.41 mmol) is purified by chiral supercritical fluid chromatography (SFC)

on a Chiralcel® OD-H column using $CO_2$ (100 bar) and MeOH with 0.2% DMEA, column size 5 μm, 2*25 cm, flow rate of 65 mL/min, UV detection 215 nm, and loading of 60 mg/injection (each 5.1 min) to give the title compound, RT=2.4 min, (5.5 g, 38%) as a yellow solid. ES/MS (m/z) 256 (M+1), $^1$H NMR (300.16 MHz, $d_6$-DMSO) δ 12.62-12.60 (m, 1H), 7.82 (dd, J=1.5, 10.2 Hz, 1H), 7.62 (dd, J=1.5, 8.1 Hz, 1H), 7.42-7.34 (m, 1H), 4.52 (t, J=7.7 Hz, 1H), 2.73 (d, J=1.8 Hz, 1H), 2.07 (dd, J=8.1, 11.7 Hz, 1H), 1.25 (s, 6H).

Example 50

4-(6,6-Dimethyl-4,5-dihydro-1H-cyclopenta[c]pyrazol-4-yl)-3-fluoro-benzonitrile, isomer 2

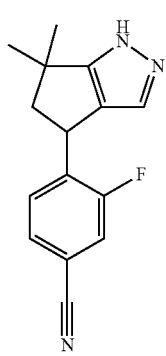 [SMILES: CC1(C)CC(c2ccc(C#N)cc2F)c2cn[nH]c21]

4-(6,6-Dimethyl-4,5-dihydro-1H-cyclopenta[c]pyrazol-4-yl)-3-fluoro-benzonitrile isomer 2 is isolated using the described chiral chromatography conditions for isomer 1. ES/MS (m/z) 256 (M+1).

Example 51

(+/−)-4-[6,6-Dimethyl-4,5-dihydro-1H-cyclopenta[c]pyrazol-4-yl]benzonitrile hydrochloride

To (+/−)-4-[(2Z)-2-(dimethylaminomethylene)-4,4-dimethyl-3-oxo-cyclopentyl]benzonitrile (3.2 g, 20 mmol) in ethanol (100 mL) and acetic acid (4 drops) is added hydrazine hydrochloride (4.17 g, 60 mmol) and the reaction is heated to 80° C. for three hours. The reaction is then cooled to room temperature and concentrated in vacuo. The residue is partitioned between ethyl acetate and saturated sodium bicarbonate solution. The layers are separated and the organic is washed with brine, dried over sodium sulfate, filtered, and concentrated in vacuo. The residue is purified by silica gel flash chromatography eluting with 1:2 ethyl acetate:pet ether. The resulting material is treated with HCl in ethyl acetate to provide the title compound (2.3 g, 70%). ES/MS (m/z) 238.2 (M+1).

Example 52

(+/−)-4-[4,5,6,7-Tetrahydro-2H-indazol-4-yl]benzonitrile

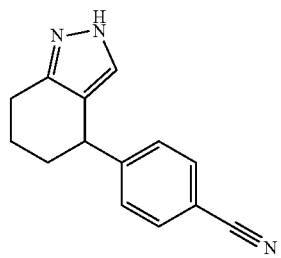 [SMILES: N#Cc1ccc(C2CCCc3n[nH]cc32)cc1]

4-(6,7-dihydro-2H-indazol-4-yl)benzonitrile (3.21 g, 14.5 mmol) is added to THF (10 mL), MeOH (10 mL), and 5% Pd/C (0.2 g) and hydrogenated under a balloon of $H_2$ at room temperature for two hours. The mixture is filtered through a pad of diatomaceous earth and evaporated to dryness. The residue is purified by silica gel flash chromatography eluting with 50%-70% ethyl acetate/hexanes, to give the title compound (3.15 g, 97%).

Example 53

4-[(4R)-4,5,6,7-Tetrahydro-2H-indazol-4-yl]benzonitrile

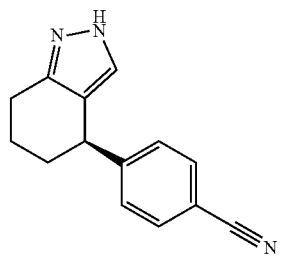 [SMILES: N#Cc1ccc([C@H]2CCCc3n[nH]cc32)cc1]

The racemic mixture is purified by chiral chromatography (Chiralpak AD-H, 0.46×15 cm 100% MeOH/0.2% DMEA, 0.6 mL/min, 250 nm) to give the title compound (1.19 g, 38%) as the second eluting isomer Tr=3.21 min. ES/MS m/z 224 (M+H). ES/MS (m/z) 224.0 (M+1).

The following Examples are prepared essentially by the method of 4-[(4R)-4,5,6,7-tetrahydro-2H-indazol-4-yl]benzonitrile.

TABLE 14

| Ex # | Chemical Name | Structure | ES/MS (m/z) (M + 1) |
|---|---|---|---|
| 54 | 4-(p-Tolyl)-4,5,6,7-tetrahydro-2H-indazole-isomer 2[a] | 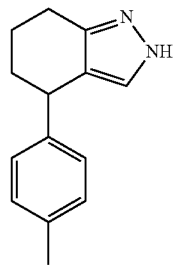 [SMILES: Cc1ccc(C2CCCc3n[nH]cc32)cc1] | 213 |
| 55 | 4-(4-Methoxyphenyl)-4,5,6,7-tetrahydro-2H-indazole-isomer 2[b] | 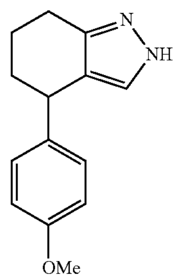 [SMILES: COc1ccc(C2CCCc3n[nH]cc32)cc1] | 229 |

[a]Chiral chromatography conditions: (4.6 × 150 mm, Chiralcel ® OJ-H, 100% MeOH, 0.2% DMEA, 1.0 mL/min, 225 nm, 2nd eluting enantiomer, Tr = 3.726 min)
[b]Chiral chromatography conditions: (4.6 × 150 mm, Chiralcel ® AD-H, 100% EtOH, 0.2% DMEA, 1.0 mL/min, 225 nm, 2nd eluting enantiomer, Tr = 3.289 min).

Example 56

4-(4-Chlorophenyl)-4,5,6,7-tetrahydro-2H-indazole isomer 2

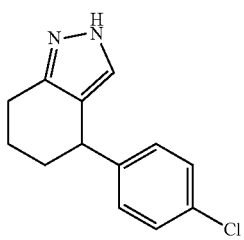 [SMILES: Clc1ccc(C2CCCc3n[nH]cc32)cc1]

4-(4-Chlorophenyl)-2-(p-tolylsulfonyl)-4,5,6,7-tetrahydroindazole (0.4 g, 1.04 mmol) is added to a solution of KOH (0.29 g, 5.21 mmol) in MeOH (25 mL) and the solution is heated to 65° C. for 2 hours. The solution is cooled to ambient temperature, the solvent removed under reduced pressure and the resulting solid diluted with water. HCl is added to pH 4, the mixture is extracted with ethyl acetate, the layers are separated and the aqueous layer is re-extracted with ethyl acetate. The organic layers are combined, dried over $Na_2SO_4$, filtered, and concentrated to dryness. The residue is purified by chiral chromatography (Chiralpak AD-H, 4.6×150 mm, 100% EtOH 0.2% DMEA, 225 mm, Tr=3.318 min) to give the title compound (93 mg, 38%) as the second eluting isomer. ES/MS m/z 234 (M+H).

Example 57

3-Methyl-4-(4,5,6,7-tetrahydro-1H-indazol-4-yl)benzonitrile-isomer 2

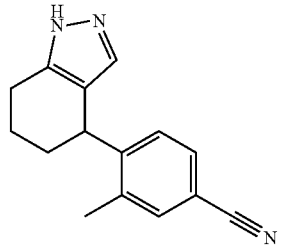 [SMILES: Cc1cc(C#N)ccc1C1CCCc2[nH]ncc21]

3-Methyl-4-(1-tetrahydropyran-2-yl-4,5,6,7-tetrahydroindazol-4-yl)benzonitrile or 3-methyl-4-(2-tetrahydropyran-2-yl-4,5,6,7-tetrahydroindazol-4-yl)benzonitrile (0.16 g, 0.5 mmol) and $H_2SO_4$ (0.11 mL, 1.99 mmol) are added to $CH_3CN$ (5.0 mL) and the solution is stirred at room temperature for 24 hours. Aqueous $Na_2CO_3$ is added until basic pH. This is diluted with ethyl acetate, the layers are separated, and the aqueous layer back extracted with ethyl acetate (3×). The organics are combined, dried over $Na_2SO_4$, filtered, and concentrated to dryness. The residue is purified by silica gel flash chromatography eluting with 6:4 hexanes/ethyl acetate to give the racemic mixture (0.088 g, 73%). The single enantiomer is obtained by chiral chromatography (Chiralpak AD-H, 4.6×150 mm, 100% EtOH 0.2% DMEA, 225 mm, Tr=4.168 min) to give the title compound (0.032 g, 27%) as the second eluting isomer. ES/MS m/z 238 (M+H).

The following Example is prepared essentially by the method of 3-methyl-4-(4,5,6,7-tetrahydro-1H-indazol-4-yl)benzonitrile isomer 2.

TABLE 15

| Ex # | Chemical Name | Structure | ES/MS (m/z) (M + 1) |
|---|---|---|---|
| 58 | 2-Methoxy-4-(4,5,6,7-tetrahydro-1H-indazol-4-yl)benzonitrile, isomer 2[a] | 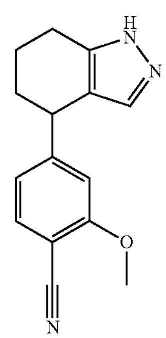 [SMILES: COc1cc(C2CCCc3[nH]ncc32)ccc1C#N] | 254 |

[a]Purification of enantiomers by chiral chromatography (Chiralcel ® AD-H, 4.6 × 150 mm, 100% MeOH, 0.2% DMEA, 1.0 mL/min, 225 nm, 2nd eluting enantiomer, Tr = 3.608 min)

Example 59

(+/−)-2-Fluoro-4-(4,5,6,7-tetrahydro-1H-indazol-4-yl)benzonitrile

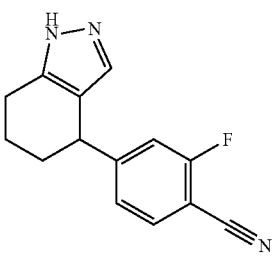 [SMILES: N#Cc1ccc(C2CCCc3[nH]ncc32)cc1F]

4-(6,7-Dihydro-1H-indazol-4-yl)-2-fluoro-benzonitrile (0.102 g, 0.43 mmol) 5% Pd/C wt/wt % (0.04 g) is added to MeOH (5.0 mL) and the mixture is stirred under 45-35 psi of hydrogen for 3 hours. The mixture is filtered through a plug of diatomaceous earth and concentrated to dryness. The residue is purified by silica gel chromatography eluting with 1:1 hexanes/ethyl acetate to give the title compound (0.021 g, 18%). ES/MS m/z 242 (M+H).

Example 60

(+/−)-(trans)-4-[7-Methyl-4,5,6,7-tetrahydro-2H-indazol-4-yl]benzonitrile

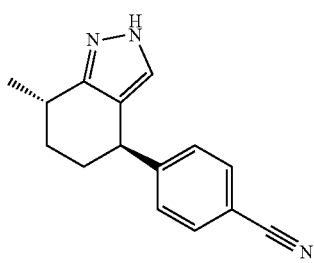 [SMILES: C[C@H]1CC[C@H](c2ccc(C#N)cc2)c2c[nH]nc21]

(+/−)-(trans)-4-(4-Methyl-3-oxo-cyclohexyl)benzonitrile (0.55 g, 2.58 mmol) is added to toluene (10.0 mL) and tert-butoxybis(dimtheylamino)methane (0.67 mL, 3.22 mmols) and stirred at 120° C. for 16 hours. The mixture is cooled to room temperature and concentrated in vacuo. The residue is added to MeOH (10.0 mL) and hydrazine (0.07 mL, 2.32 mmol) and stirred at 80° C. for 1.0 hour. The mixture is cooled to room temperature and concentrated in vacuo. The residue is purified by silica gel chromatography (35%-55% EtOAc/hexanes) to give (+/−)-(trans)-4-[7-methyl-4,5,6,7-tetrahydro-2H-indazol-4-yl]benzonitrile (0.18 g, 29%).

Example 61

4-[7-Methyl-4,5,6,7-tetrahydro-2H-indazol-4-yl]benzonitrile-isomer 2

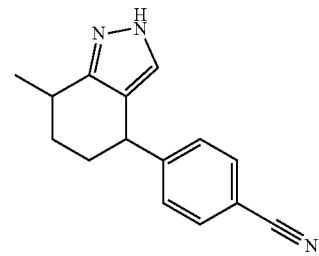 [SMILES: CC1CCC(c2ccc(C#N)cc2)c2c[nH]nc21]

and

Example 62

4-[7-Methyl-4,5,6,7-tetrahydro-2H-indazol-4-yl]benzonitrile-isomer 4

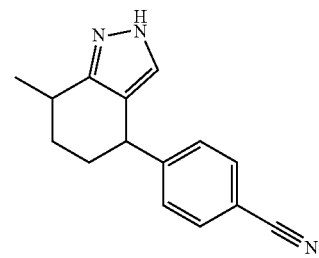 [SMILES: CC1CCC(c2ccc(C#N)cc2)c2c[nH]nc21]

(+/−)-(cis/trans)-4-[7-Methyl-4,5,6,7-tetrahydro-2H-indazol-4-yl]benzonitrile (0.36 g, 1.52 mmol) and (+/−)-(trans)-4-[7-methyl-4,5,6,7-tetrahydro-2H-indazol-4-yl]benzonitrile (0.18 g, 0.76 mmol) are combined and the single enantiomers are obtained by chiral chromatography (Chiralpak AD-H, 4.6×150 mm, 100% EtOH 0.2% DMEA, 225 mm) to give (cis)-4-[7-methyl-4,5,6,7-tetrahydro-2H-indazol-4-yl]benzonitrile-isomer 2, (0.05 g, 27%) as the second eluting isomer. ES/MS m/z 238 (M+H), Tr=2.988 min. (trans)-4-[7-Methyl-4,5,6,7-tetrahydro-2H-indazol-4-yl]benzonitrile-isomer 4, Example 61 (0.07 g, 19%). ES/MS m/z 238 (M+H).

Example 63

(+/−)-4-(7,7-Dimethyl-2,4,5,6-tetrahydroindazol-4-yl)-3-methyl-benzonitrile hydrochloride

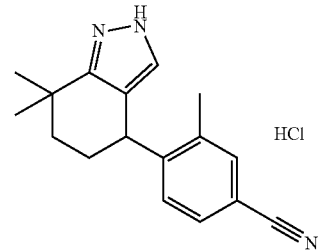 [SMILES: Cc1cc(C#N)ccc1C1CCC(C)(C)c2n[nH]cc21 ; Cl]

4-(4,4-Dimethyl-3-oxo-cyclohexyl)-3-methyl-benzonitrile (0.6 g, 2.49 mmol) in N,N-dimethylformamide dimethylacetal (50 mL) is stirred at 90° C. for two days. The mixture is cooled to room temperature and concentrated in vacuo. The residue is diluted with ethyl acetate (50 mL) and water (50 mL). The organic phase is separated and the aqueous phase is extracted with ethyl acetate (3×50 mL). The combined organic phase is washed with brine, dried over anhydrous sodium sulfate, and concentrated in vacuo. The residue is purified by silica gel flash chromatography, eluting with pet ether:EtOAc 1:1 to MeOH:DCM=1:30 to give 4-[(2Z)-2-(dimethylaminomethylene)-4,4-dimethyl-3-oxo-cyclohexyl]-3-methyl-benzonitrile (0.2 g, 27%).

Hydrazine hydrochloride (0.14 g, 2 mmol) is added to 4-[(2Z)-2-(dimethylaminomethylene)-4,4-dimethyl-3-oxo-cyclohexyl]-3-methyl-benzonitrile (0.2 g, 0.67 mmol) in ethanol (30 mL), then acetic acid (two drops) is added to the mixture. After the addition is complete, the reaction mixture is stirred at 80° C. for 3 h. The mixture is cooled to room temperature and concentrated in vacuo. The residue is diluted with ethyl acetate (50 mL) and saturated sodium bicarbonate solution (50 mL). The organic phase is separated and the aqueous phase extracted with ethyl acetate (3×50 mL). The combined organic phase is washed with brine, dried over anhydrous sodium sulfate, and concentrated in vacuo. The residue is purified by silica gel column chromatography (eluted with pet ether:EtOAc=2:1 to 1:1) to give the title compound. The product is added to HCl/ethyl acetate and concentrated in vacuo to give the HCl salt of the title compound (0.12 g, 67%). ES/MS 266 (M+H).

Example 64

4-(7,7-Dimethyl-2,4,5,6-tetrahydroindazol-4-yl)-3-methyl-benzonitrile, isomer 2

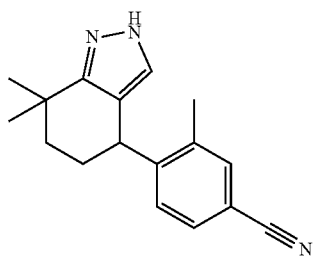 [SMILES: Cc1cc(C#N)ccc1C1CCC(C)(C)c2n[nH]cc21]

The single enantiomer is obtained by chiral chromatography (Chiralpak AD-H, 4.6×150 mm, 3:2 MeOH/CH3CN 0.2% isopropylamine, 225 mm, 1.0 mL/min, Tr=3.503 min) to give the title compound (0.038 g, 31%) as the second eluting isomer. ES/MS m/z 266 (M+H).

The following Examples are prepared essentially by the method of 3-methyl-4-(4,5,6,7-tetrahydro-1H-indazol-4-yl)benzonitrile.

TABLE 16

| Ex # | Chemical Name | Structure | ES/MS (m/z) (M + 1) |
|---|---|---|---|
| 65 | (+/−)-4-(7,7-Dimethyl-2,4,5,6-tetrahydro-indazol-4-yl)-3-fluoro-benzonitrile hydrochloride | 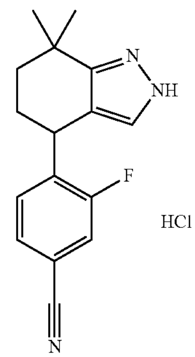 [SMILES: CC1(C)CCC(c2ccc(C#N)cc2F)c2c[nH]nc21 ; Cl] | 270 |
| 66 | 4-(7,7-Dimethyl-2,4,5,6-tetrahydroindazol-4-yl)-3-fluoro-benzonitrile-isomer 2[a] | 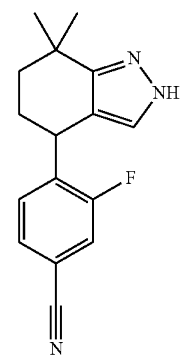 [SMILES: CC1(C)CCC(c2ccc(C#N)cc2F)c2c[nH]nc21] | 270 |
| 67 | (+/−)-4-(7,7-Dimethyl-2,4,5,6-tetrahydroindazol-4-yl)-2-fluoro-benzonitrile[b] | 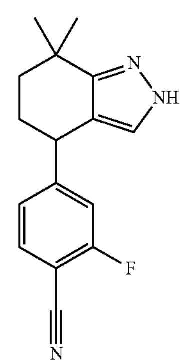 [SMILES: CC1(C)CCC(c2ccc(C#N)c(F)c2)c2c[nH]nc21] | 270 |

[a] Purification of enantiomers by chiral chromatography (Chiralcel ® AD-H, 4.6 × 150 mm, 100% MeOH, 0.2% isopropylamine, 1.0 mL/min, 225 nm, 2nd eluting enantiomer, Tr = 4.175 min).

[b] Step 1-Use tert-butoxybis(dimethylamino)methane (1.0 eq) in toluene at 120° C. for 26 hours.

Reagents employed in the following assays are readily available from commercial sources or can be readily synthesized by one skilled in the art. Comparator compounds used herein are fadrozole and LCI699. Fadrozole is an aromatase inhibitor marketed by Novartis Corporation in Japan for the treatment of breast cancer under the trade name AFEMA® (trademark of Novartis Corporation); (www.righthealth.com/topic/Fadrozole visited May 26, 2011). LCI 699 is an investigational drug being developed by Novartis Corporation (Thompson Reuters Pharma Drug Report LCI699, ©Thompson Reuters 2011). Structural representations for fadrozole and LCI699 are as shown below.

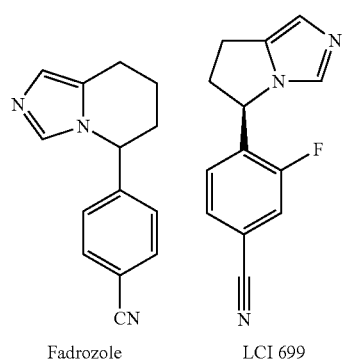

Fadrozole           LCI 699

Aldosterone Synthase Inhibitor Assay

Chinese hamster fibroblast cells (V79, ATCC™) constitutively expressing human cyp11B2 are established by transfection with a mammalian expression vector harboring the human cyp11B2 cDNA under CMV promoter and a neomycin antibiotic resistant gene for selection in mammalian cells. V79 cells are transfected in T225 $cm^2$ flasks with the lipofectamine transfection reagent and the human cyp11B2 cDNA. Positive clones are selected with the selection antibiotic geneticin at 1 mg/mL.

Aldosterone production from transfected cells is initiated by the addition of 1 μM DOC in the medium. After 24 hours incubation, 100 μL cell culture medium is collected and aldosterone concentration in the medium is determined using a liquid chromatography-mass spectrometry (LC-MS) method. The medium is first extracted using a Beckman Coulter FX liquid handling system (modified for use of organic solvents) with a 96-tip head to add an internal standard (IS) solution to each well (10 μL of 100 ng/mL d7-aldosterone, (C/D/N Isotopes, Inc. Quebec, Canada), in 15% ACN/water). The wells are then extracted 3× with EtOAc (150 μl) using the FX, combining the organic layers in a new 96-well plate. The solvent is dried in a GeneVac HT-4 or under nitrogen. The FX is then used to reconstitute the samples in 15% ACN/water (60 μl) and the plates are heat-sealed. The LC-MS method employs an Agilent LC with a binary pump to produce a gradient of water and ACN, each containing 0.1% formic acid, with a flow rate of 1 mL/min over a Betasil 2.1×10 mm C18 column. A 25 μl aliquot of the sample is injected and a gradient from 20-100% ACN+0.1% formic acid (FA) in 1 min is initiated. Aldosterone elutes at 0.7 min. Starting conditions are held for 1 minute to re-equilibrate the column. An ABI 4000 tandem mass spectrometer is used for MS/MS analysis in the negative ion mode. The MS/MS method monitors two multiple reaction monitoring (MRM) transitions for aldosterone (359.19/331.09 & 359.19/188.8) and two for the IS (367.19/339.3 & 367.19/194.1). The area under the peak from each transition is added together to comprise the signal from aldosterone and IS, respectively. The ratio of these areas is compared to the controls from each plate to give a % inhibition value for each sample. The detection limit for aldosterone is 40 μg/mL.

To determine the inhibition of aldosterone production by a test compound, V79-hcyp11B2 cells are seeded in a 96-well plate at 20,000 cells per well. DOC and various concentrations of test compounds in 1:3 dilution increments are added to the cell culture medium. After 24 hours incubation, 100 μl of cell medium are collected and aldosterone concentration determined as described above. Data are fit to a 4 parameter-fit logistics curve to determine $IC_{50}$ values.

The Examples of the invention demonstrate potent aldosterone synthase inhibition with $IC_{50}$s of about ≤0.900 μM. Representative compounds are shown in Table 1.

TABLE 17*

| Example | $IC_{50}$ (hcyp11B2, μM) |
|---|---|
| 1 | 0.005, n = 4 |
| 59 | 0.005, n = 4 |
| 49 | 0.007, n = 2 |
| 54 | 0.154, n = 2 |
| 18 | 0.157 |
| Fadrozole | 0.018, n = 63 |
| Novartis LCI699 | 0.0076, n = 10 |

*These data are the results from separate experiments. The above data expressed as a geometric means show that Examples of the invention are potent aldosterone synthase inhibitors in vitro.

Inhibition of Aldosterone Synthase in Rats

The effect of compounds on aldosterone production in rats is assessed using the rat sodium-deficiency diet model. Studies are conducted using male Sprague Dawley rats, aged 6-7 weeks, and approximately 175-190 grams (Harlan Laboratories, Indianapolis, Ind., USA). Rats are singly housed under normal light cycle (12 hours light and 12 hours dark) and received diet (Harlan Teklad 90228 Sodium Deficient Diet) and water ad libitum. Rats are randomized by body weight and placed on Teklad 90228 for 7 days. On Day 7 rats are orally dosed at 10 mL/kg with vehicle (1% hydroxy ethyl cellulose (HEC)/0.25% Tween80/0.05% antifoam (AF), or Acacia 10% w/v/Antifoam 1510-US 0.05% v/v deionized water (DIW)), positive control (1 mg/Kg, Fadrozole), or test compound. At 3 hours post dose rats are bled (~0.5 mL) from the ocular orbit under isoflurane anesthesia. At 6 hours post-dose the rats are euthanized with $CO_2$ and bled by cardiac puncture. Blood samples are clotted at least 30 minutes and serum is prepared and stored at approximately −80° C. until assayed. Aldosterone, steroids, and compound exposure are analyzed by mass spectroscopy.

The effect of Examples 1 and 49 on aldosterone production in the rat Na-deficient diet model is illustrated in Table 18 below.

TABLE 18

| Example | Dose (mg/kg) | Aldosterone (pg/mL) 3 hrs | Aldosterone (pg/mL) 6 hrs | % Inhibition 3 hrs | % Inhibition 6 hrs |
|---|---|---|---|---|---|
| vehicle | 0.0 | 1881.7 | 2556.7 | 0.0 | 0.0 |
| 1 | 10.0 | 973 | 1380 | 48 | 46 |
| 49 | 30.0 | 1008 | 1704 | 46 | 33 |
| Fadrozole | 1.0 | 669.8 | 1144.2 | 64.4 | 55.2 |

The data show that the Examples 1 and 49 inhibit aldosterone production in vivo.

Cortisol Inhibition Assay

Chinese hamster fibroblast cells (V79) constitutively expressing human cyp11B1 are established by transfection with a mammalian expression vector harboring the human cyp11B1 cDNA under CMV promoter and a neomycin antibiotic resistant gene for selection in mammalian cells. V79 cells are transfected in T225 $cm^2$ flasks with the lipofectamine transfection reagent and the human cyp11B1 cDNA. Positive clones are selected with the selection antibiotic geneticin at 1 mg/mL. Cortisol production from transfected cells is initiated by the addition of 1 µM 11-deoxycortisol in the medium. After 24 hours incubation, culture medium is collected and cortisol concentration in the medium is determined using a liquid chromatography-mass spectrometry (LC-MS) method. The cell media (100 µL) is transferred to a new deep-well 96-well plate. A Beckman Coulter FX liquid handling system (modified for use with organic solvents) with a 96-tip head is used to add an IS solution to each well (10 µl of 200 ng/mL d-4-cortisol). The wells are then extracted 3× with EtOAc (300 µl) using the FX, combining the organic layers in a new deep-well 96-well plate. The solvent is then dried in a GeneVac HT-4 or under nitrogen. The FX is then used to reconstitute the samples in 50% MeOH/water (100 µl) and the plates are heat-sealed.

An HPLC with two pumps produces a gradient of water (containing 0.1% formic acid) and MeOH with a flow rate of 0.6 mL/min over an Xbridge Shield RP18, 3.5 micron, 2.1×50 mm column with a 2.1×10 mm guard column of the same material in a 5 micron particle size. A 40 µl aliquot of the sample is injected and a gradient from 20-100% MeOH in 0.95 min is initiated. Cortisol elutes at 0.8 min. Starting conditions are then held for 1 minute to re-equilibrate the column. An ABI QTRAP 4000 tandem mass spectrometer is used for MS/MS analysis in the positive ion mode. The MS/MS methods monitor transitions for the cortisol and IS at 363.0/121.0 and 367.3/121.0 respectively. These are respectively integrated to give the peak areas. The cortisol/IS area-ratio is used to determine cortisol concentration by comparison to a standard curve. The detection limit for cortisol is 1 ng/mL.

To determine the inhibition of cortisol production by a test compound, V79-human cyp11B1 cells are seeded in a 96-well plate at 20,000 cells per well. 11-Deoxycortisol and various concentrations of test compounds in 1:3 dilution increments are added to the cell culture medium. After 24 hours incubation, 100 µl of cell medium are collected and cortisol concentration determined as described above. Data are fit to a 4 parameter-fit logistics curve to determine $IC_{50}$ values.

The Examples of the invention demonstrate modest potency in inhibiting cortisol production from V79-hcyp11B1 cells compared to comparator compounds as shown in Table 19. The relative selectivity of inhibiting aldosterone production versus that of inhibiting cortisol production is calculated using the equation: Selectivity Ratio=$IC_{50}$(hcyp11B1)/$IC_{50}$(hcyp11B2).

TABLE 19*

| Example | $IC_{50}$ (hcyp11B1, µM) | Selectivity Ratio |
|---|---|---|
| 1 | 0.165, n = 5 | 33.0 |
| 49 | 0.311, n = 2 | 44.4 |
| Fadrozole | 0.069, n = 61 | 3.7 |
| Novartis LCI699 | 0.035, n = 10 | 4.6 |

*These data are the results from separate experiments. These data demonstrate that Examples 1 and 49 exhibit greater selectivity in the inhibition of aldosterone relative to cortisol inhibition than the comparator compounds.

Testosterone and Estradiol Production Assay

The human adrenocarcinoma cell line H295R is used to monitor the production of testosterone and estradiol in vitro. Cells seeded in 96-well plate at 50,000 cells per well and cultured in DMEM medium supplemented with 2.5% Nuse-rum. Various concentrations of test compounds in 1:3 dilution increments are added to the cell culture medium. After incubation for 48 hours, 100 µl culture medium is collected and d5-estradiol and d3-testosterone are added as ISs for estradiol and testosterone respectively.

An equal volume of sodium carbonate/sodium bicarbonate buffer (0.5 mol/L, pH 9.4) is added to the samples followed by freshly prepared dansyl chloride solution (50 µl, 20 mg/mL). Samples are mixed and incubated for 60 min at 60° C. The samples are then extracted 3× with EtOAc (300 nl) using the FX, combining the organic layers in a new deep-well 96-well plate. The solvent is then dried in a GeneVac HT-4 or under nitrogen. The FX is used to reconstitute the samples in 50% MeOH/water (100 nl) and the plates are heat-sealed.

An HPLC with two pumps produces a gradient of water (containing 0.1% formic acid) and MeOH with a flow rate of 0.6 mL/min over an Xbridge Shield RP18, 3.5 micron, 2.1×50 mm column with a 2.1×10 mm guard column of the same material in a 5 micron particle size. A 40 µl aliquot of the sample is injected and a gradient from 20-100% MeOH in 0.95 min is initiated. An ABI QTRAP 4000 tandem mass spectrometer is used for MS/MS analysis in the positive ion mode. The MS/MS methods monitor transitions for testosterone (289/97), estradiol (506.3/171.0), and their respective ISs 292/109 and 511.3/171.0. These peaks are separately integrated to give the peak areas. The area ratios of testosterone/IS and estradiol/IS are used to determine testosterone and estradiol concentrations by comparison to their respective standard curves. The detection limits for testosterone and estradiol are 0.1 ng/mL and 0.01 ng/mL respectively.

Examples 1 and 49 demonstrate weak inhibition of testosterone and estradiol production from H295R cells. The results are shown in Table 20 along with the relative selectivity for aldosterone compared to testosterone or estradiol for each compound.

TABLE 20*

| Example | Testosterone $IC_{50}$ (µM) | Estradiol $IC_{50}$ (µM) | Selectivity ratio for aldosterone compared with testosterone | Selectivity ratio for aldosterone compared with estradiol |
|---|---|---|---|---|
| 1 | >30, n = 4 | 13.2, n = 3 | >6000 | 2640 |
| 49 | >30, n = 5 | 22.0 | >4285 | 3143 |
| Fadrozole | 1.54 | <0.0015 | 82 | 0.08 |
| Novartis LCI699 | 5.01, n = 2 | 0.123, n = 2 | 663 | 16.3 |

*Tests were not performed simultaneously for Examples of Table 20 and comparator compounds.

Cynomolgus Monkey Aldosterone Inhibition Assay

Chinese hamster fibroblast cells (V79) constitutively expressing cynomolgus monkey cyp11B2 is established by transfection with a mammalian expression vector harboring the cynomolgus monkey cyp11B2 cDNA. This cell line was used to measure the activity of compounds in inhibiting aldosterone production from cynomolgus monkey enzyme. Cell culture condition and aldosterone detection method is performed following the same protocol described in the "Aldosterone inhibition assay". Example 1 and Example 49 display relative $IC_{50}$ values of 0.00246 and 0.0041 µM in the cynomolgus monkey aldosterone inhibition assay respectively (n=1).

Cynomolgus Monkey Cortisol Inhibition Assay

Chinese hamster fibroblast cells (V79) constitutively expressing cynomolgus monkey cyp11B1 is established by transfection with a mammalian expression vector harboring the cynomolgus monkey cyp11B1 cDNA. This cell line was used to measure the activity of compounds in inhibiting aldosterone production from cynomolgus monkey enzyme. Cell culture condition and cortisol detection method is performed following the same protocol described in the "cortisol inhibition assay". Example 1 and Example 49 display relative $IC_{50}$ values of 0.209 and 0.579 μM in the cynomolgus monkey cortisol inhibition assay respectively (n=1).

We claim:

1. A compound of the formula:

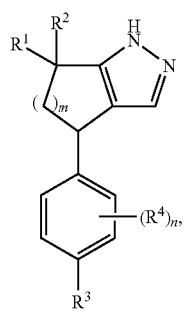

wherein
n is 0 or 1;
m is 1 or 2;
$R^1$ and $R^2$ are independently selected from hydrogen, —$CH_3$, and —$CH_2CH_3$;
$R^3$ is —CN;
$R^4$ is at each instance independently selected from —F, —Cl, —Br, —$CH_3$, and —$OCH_3$;
or a pharmaceutically acceptable salt thereof.

2. A compound of the formula:

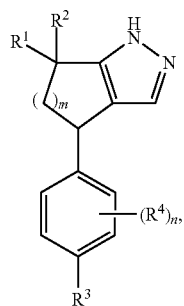

wherein
n is 0, 1, or 2;
m is 1 or 2;
$R^1$ and $R^2$ are independently selected from hydrogen and —$CH_3$;
$R^3$ is —F or —Cl;
$R^4$ is at each instance independently selected from —F, —Cl, —Br, —$CH_3$, and —$CF_3$;
or a pharmaceutically acceptable salt thereof.

3. A compound of claim 1 of the formula:

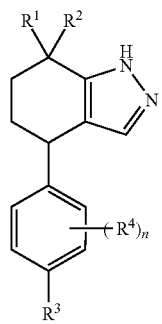

wherein
n is 0 or 1;
$R^1$ and $R^2$ are independently selected from hydrogen and —$CH_3$;
$R^3$ is hydrogen, —CN, —Cl, —$OCH_3$, or —$CH_3$;
$R^4$ is at each instance independently selected from —F, —$CH_3$, and —$OCH_3$;
or a pharmaceutically acceptable salt thereof.

4. A compound of claim 1 wherein m is 1; $R^1$ and $R^2$ are —$CH_3$; $R^3$ is —CN; n is 0 or 1; $R^4$ is —F, or a pharmaceutically acceptable salt thereof.

5. A compound of claim 1 wherein the compound is 4-(6,6-dimethyl-4,5-dihydro-1H-cyclopenta[c]pyrazol-4-yl)-benzonitrile:

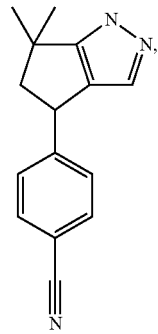 [SMILES: CC1(C)CC(c2ccc(C#N)cc2)c2cn[nH]c21]

or a pharmaceutically acceptable salt thereof.

6. A compound of claim 5 wherein the compound is 4-[(4R)-(6,6-dimethyl-4,5-dihydro-1H-cyclopenta[c]pyrazol-4-yl)]benzonitrile:

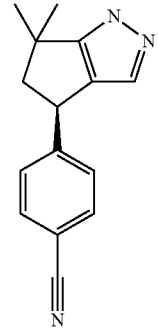 [SMILES: CC1(C)C[C@H](c2ccc(C#N)cc2)c2cn[nH]c21]

or a pharmaceutically acceptable salt thereof.

7. A compound of claim 6 wherein the compound is 4-[(4R)-(6,6-dimethyl-4,5-dihydro-1H-cyclopenta[c]pyrazol-4-yl)]benzonitrile:

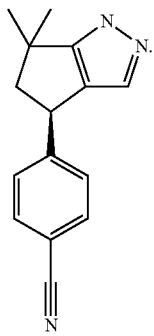 [SMILES: CC1(C)C[C@H](c2ccc(C#N)cc2)c2cn[nH]c21]

8. A compound of claim 1 wherein the compound is 4-(6,6-dimethyl-4,5-dihydro-1H-cyclopenta[c]pyrazol-4-yl)-3-fluoro-benzonitrile:

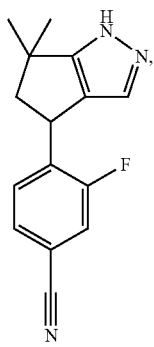 [SMILES: CC1(C)CC(c2ccc(C#N)cc2F)c2cn[nH]c21]

or a pharmaceutically acceptable salt thereof.

9. A compound of claim 8 wherein the compound is 4-(6,6-dimethyl-4,5-dihydro-1H-cyclopenta[c]pyrazol-4-yl)-3-fluoro-benzonitrile:

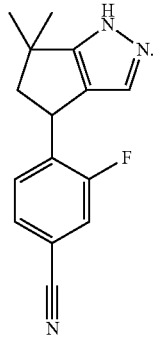 [SMILES: CC1(C)CC(c2ccc(C#N)cc2F)c2cn[nH]c21]

10. A pharmaceutical composition comprising a compound according to claim 1, or a pharmaceutically acceptable salt thereof, and one or more pharmaceutically acceptable carriers, diluents, or excipients.

11. A pharmaceutical composition comprising a compound according to claim 4, or a pharmaceutically acceptable salt thereof, and one or more pharmaceutically acceptable carriers, diluents, or excipients.

12. A pharmaceutical composition comprising a compound according to claim 5, or a pharmaceutically acceptable salt thereof, and one or more pharmaceutically acceptable carriers, diluents, or excipients.

13. A method for treating chronic kidney disease comprising administering an effective amount of a compound of claim 1, or a pharmaceutically acceptable salt thereof to a patient in need thereof.

14. A method for treating chronic kidney disease comprising administering an effective amount of a compound of claim 4, or a pharmaceutically acceptable salt thereof to a patient in need thereof.

15. A method for treating chronic kidney disease comprising administering an effective amount of a compound of claim 5, or a pharmaceutically acceptable salt thereof to a patient in need thereof.

16. A method for treating diabetic nephropathy comprising administering an effective amount of a compound of claim 1, or a pharmaceutically acceptable salt thereof to a patient in need thereof.

17. A method for treating diabetic nephropathy comprising administering an effective amount of a compound of claim 4, or a pharmaceutically acceptable salt thereof to a patient in need thereof.

18. A method for treating diabetic nephropathy comprising administering an effective amount of a compound of claim 5, or a pharmaceutically acceptable salt thereof to a patient in need thereof.

* * * * *

UNITED STATES PATENT AND TRADEMARK OFFICE
CERTIFICATE OF CORRECTION

| | |
|---|---|
| PATENT NO. | : 8,778,984 B2 |
| APPLICATION NO. | : 13/490530 |
| DATED | : July 15, 2014 |
| INVENTOR(S) | : Bell et al. |

Page 1 of 1

It is certified that error appears in the above-identified patent and that said Letters Patent is hereby corrected as shown below:

In the Claims

Column 56, lines 29-30, Claim 5, please delete "yl)-benzonitrile:" and insert --yl)benzonitrile:--, therefor.

Signed and Sealed this
Seventh Day of October, 2014

Michelle K. Lee
*Deputy Director of the United States Patent and Trademark Office*